(12) United States Patent
Heitsch et al.

(10) Patent No.: US 6,410,573 B1
(45) Date of Patent: Jun. 25, 2002

(54) 2,5-SUBSTITUTED BENZOLSULFONYLUREAS AND THIOUREAS METHODS FOR THE PRODUCTION THEREOF USE THEREOF AND PHARMACEUTICAL PREPARATIONS CONTAINING THE SAME

(75) Inventors: Holger Heitsch, Mainz-Kastel; Heinrich Christian Englert, Hofheim; Heinz Gögelein, Frankfurt am Main, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/743,715

(22) PCT Filed: Jul. 3, 1999

(86) PCT No.: PCT/EP99/04643

§ 371 (c)(1), (2), (4) Date: Jan. 16, 2001

(87) PCT Pub. No.: WO00/03978

PCT Pub. Date: Jan. 27, 2000

(30) Foreign Application Priority Data

Jul. 16, 1998 (DE) ......................... 198 32 009

(51) Int. Cl.$^7$ .................. A61K 31/44; A61K 31/38; A61K 31/34; A61K 31/175; C07D 333/22

(52) U.S. Cl. .................. 514/357; 514/438; 514/461; 514/592; 549/77; 549/496; 546/331; 546/332; 564/47

(58) Field of Search .................. 546/47, 331, 332; 514/592, 357, 438, 461; 549/77, 496; 564/47

(56) References Cited

U.S. PATENT DOCUMENTS

| | | | |
|---|---|---|---|
| 5,476,850 A | 12/1995 | Englert et al. ........... 514/239.5 |
| 5,574,069 A | * 11/1996 | Englert et al. ............... 514/586 |
| 5,607,976 A | 3/1997 | Englert et al. ............... 514/584 |
| 5,631,275 A | 5/1997 | Englert et al. ............... 514/423 |
| 5,633,239 A | 5/1997 | Englert et al. ................. 514/83 |
| 5,652,268 A | 7/1997 | Englert et al. ............... 514/585 |
| 5,698,596 A | 12/1997 | Englert et al. ............... 514/586 |
| 5,731,341 A | 3/1998 | Englert et al. ............... 514/416 |
| 5,776,980 A | 7/1998 | Englert et al. ............... 514/586 |
| 5,880,155 A | 3/1999 | Englert et al. ............... 514/585 |
| 5,977,177 A | 11/1999 | Englert et al. ............... 514/592 |
| 6,090,981 A | 7/2000 | Englert et al. ................. 564/86 |

FOREIGN PATENT DOCUMENTS

| | | |
|---|---|---|
| EP | 612 724 A1 | 8/1994 |
| EP | 657 423 A1 | 6/1995 |
| EP | 661 264 A1 | 7/1995 |
| EP | 726 250 A1 | 8/1996 |
| EP | 727 416 A1 | 8/1996 |
| EP | 727 417 A1 | 8/1996 |
| EP | 728 741 A1 | 8/1996 |

OTHER PUBLICATIONS

Thomas R Bailey, Unsymmetrical Heterobiaryl Synthesis. A Highly Efficient Palladium–catalyzed Cross–coupling Reaction of Heteroaryl Trialkylstannanes with Aryl Halides, Tetrahedron Letters, vol. 27, No. 37, 1986, pp. 4407–1140.

Pierre Deprez et al., Sulfonylureas and Sulfonylcarbamates as New Non–Tetrazole Angiotensin II Receptor Antagonists. Discovery of a Highly Potent Orally Active (Imidazolylbiphenylyl) sulfonylurea (HR 720), J. Med. Chem., 1995, 38, 2357–2377.

Holger Heitsch et al, 3N–Methylbiphenylsulfonylurea and –Carbamate Substituted Imidazo [4,5–b]pyridines. Potent Antaogonists of the ANG II AT, Receptors, Bioortanic & Medicinal Chemistry, vol. 5, No. 4, 1978, pp. 673–678.

Heiner Jendralla et al., Efficient, Simple Procedures for the Large–Scale Preparation of Building Blocks for Angiotensin (II) Receptor Antagonists, Liebigs Ann., 1995, pps. 1253–1257.

W. Linz et al., Carciovascular Effects of the Novel Potassium Channel Opener (3S, 4R)–3–Hydroxy–2,2–dimethyl–4–(2–oxo–1–pyrrolidinyl)–6–phenyslfonylchromane Hemihydrate, Arzneimittelforschung/Drug Research 42 (II), 1992, pps 1180–1185.

N. Miyaura et al., The Palladium–Catalyzed Cross–Coupling Reaction of Phenylbornic Acid With Haloarenes in The Presence of Bases, Synthetic Communications, 11 (7), 1981, pps 513–519.

Alfonso Gennaro, Remington's Pharmaceutical Sciences, 17$^{th}$ ed. (1985), pps 1418–1419.

P Rocca et al., A New Convergent Synthesis of alpha—Substituted—beta—Carbolines, Tetrahedron, vol. 49, No. 16, 1993, pps 3325–3342.

Hitomi Suzuki et al., Chemistry Letters, The Chemical Society of Japan, 1980, pps 1363–1364.

* cited by examiner

*Primary Examiner*—Alan L. Rotman
(74) *Attorney, Agent, or Firm*—Finnegan, Henderson, Farabow, Garrett & Dunner, LLP

(57) ABSTRACT

Novel 2,5-substituted benzolsulfonyl ureas and thioureas of formula (I) as illustrated in the disclosure. The compounds are useful active ingredients for medicaments. The compounds of formula (I) act as inhibitors on ATP-sensitive potassium canals and are suitable for the treatment of cardiovascular disorders, especially the treatment of arrhythmias, prevention of sudden death from heart disease or affect diminished contractility of the heart. The invention also relates to methods for producing compounds of formula (I), the use thereof and pharmaceutical preparations containing said compounds.

11 Claims, No Drawings

2,5-SUBSTITUTED BENZOLSULFONYLUREAS AND THIOUREAS METHODS FOR THE PRODUCTION THEREOF USE THEREOF AND PHARMACEUTICAL PREPARATIONS CONTAINING THE SAME

This application is a national stage filing under 35 U.S.C. §371 of international application no. PCT/EP99/04643, filed on Jul. 3, 1999.

The present invention relates to novel 2,5-substituted benzenesulfonylureas and -thioureas of the formula I

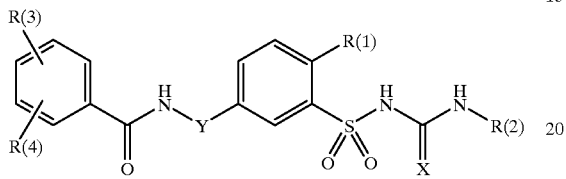

in which R(1), R(2), R(3), R(4), X and Y have the meanings indicated below, which are valuable pharmaceutical active compounds. The compounds of the formula I have an inhibitory action on ATP-sensitive potassium channels and are suitable, for example, for the treatment of disorders of the cardiovascular system, in particular for the treatment of arrhythmias, for the prevention of sudden heart death or for affecting decreased contractility of the heart. The invention furthermore relates to processes for the preparation of the compounds of the formula I, their use and pharmaceutical preparations comprising them.

A hypoglycemic action is described for certain benzenesulfonylureas. Glibenclamide, which is used therapeutically as an agent for the treatment of diabetes mellitus, counts as a prototype of hypoglycemic sulfonylureas of this type. Glibenclamide blocks ATP-sensitive potassium channels and is used in research as a tool for the exploration of potassium channels of this type. In addition to its hypoglycemic action, glibenclamide additionally possesses other actions which are attributed to the blockade of precisely these ATP-sensitive potassium channels, which as yet, however, still cannot be utilized therapeutically. These include, in particular, an antifibrillatory action on the heart. In the treatment of ventricular fibrillation or its early stages with glibenclamide, however, the hypoglycemia simultaneously produced by this substance would be undesirable or even dangerous, as it can further worsen the condition of the patient.

The patent applications EP-A-612 724, EP-A-657 423, EP-A-661 264, EP-A-726 250, EP-A-727 416, EP-A-727 417 and EP-A-728 741 disclose antifibrillatory benzenesulfonylureas and -thioureas having decreased hypoglycemic action. The properties of these compounds, however, are still not satisfactory in various respects, and there furthermore exists a need for compounds having a more favorable pharmacodynamic and pharmacokinetic property profile, which are better suited, in particular, to the treatment of a disturbed heart rhythm and its consequences. Surprisingly, it has now been found that certain 2,5-substituted benzenesulfonylureas and -thioureas which contain an unsaturated radical in the 2-position are distinguished by a marked action on ATP-sensitive potassium channels.

The present invention thus relates to compounds of the formula I

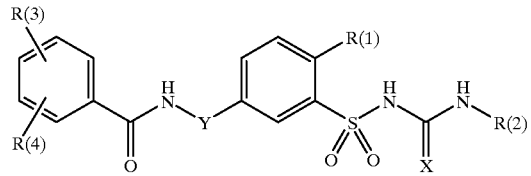

in which
X is oxygen or sulfur;
Y is —(CR(5)$_2$)$_n$—;
R(1) is
1. phenyl which is unsubstituted or is substituted by one or two identical or different substituents from the group consisting of halogen, (C$_1$–C$_4$)-alkyl, (C$_1$–C$_4$)-alkoxy, —S(O)$_m$—(C$_1$–C$_4$)-alkyl, phenyl, amino, hydroxyl, nitro, trifluoromethyl, cyano, hydroxycarbonyl, carbamoyl, (C$_1$–C$_4$)-alkoxycarbonyl and formyl; or
2. naphthyl; or
3. monocyclic or bicyclic heteroaryl having one or two identical or different ring heteroatoms from the group consisting of oxygen, sulfur and nitrogen; or
4. —S(O)$_m$-phenyl; or
5. (C$_2$–C$_5$)-alkenyl which is unsubstituted or is substituted by a radical from the group consisting of phenyl, cyano, hydroxycarbonyl and (C$_1$–C$_4$)-alkoxycarbonyl; or
6. (C$_2$–C$_5$)-alkynyl which is unsubstituted or is substituted by a radical from the group consisting of phenyl and (C$_1$–C$_4$)-alkoxy;
R(2) is hydrogen or (C$_1$–C$_3$)-alkyl;
R(3) and R(4) independently of one another are hydrogen, halogen or (C$_1$–C$_4$)-alkoxy;
the radicals R(5), which are all independent of one another and can be identical or different, are hydrogen or (C$_1$–C$_3$)-alkyl;
m is 0, 1 or 2;
n is 1, 2, 3 or 4;
in all their stereoisomeric forms and mixtures thereof in all ratios, and their physiologically tolerable salts.

If radicals, groups, substituents or variables can occur a number of times in the compounds of the formula I, they can all independently of one another have the meanings indicated and can in each case be identical or different.

The term alkyl, if not stated otherwise, denotes straight-chain or branched saturated hydrocarbon radicals. This also applies to radicals derived therefrom such as, for example, alkoxy, alkoxycarbonyl or —S(O)$_m$-alkyl. Examples of alkyl radicals are methyl, ethyl, n-propyl, isopropyl, n-butyl, sec-butyl, isobutyl or tert-butyl. Examples of alkoxy are methoxy, ethoxy, n-propoxy or isopropoxy.

Alkenyl and alkynyl represent straight-chain or branched, mono- or polyunsaturated hydrocarbon radicals, in which the double bonds and/or triple bonds can be situated in any desired positions. Examples of alkenyl and alkynyl are vinyl, prop-2-enyl (allyl), prop-1-enyl, butenyl, 3-methylbut-2-enyl, ethynyl, prop-2-ynyl (propargyl), prop-1-ynyl, but-2-ynyl and but-3-ynyl.

Halogen is fluorine, chlorine, bromine or iodine, preferably chlorine or fluorine.

In substituted phenyl radicals, the substituents can be situated in any desired positions. In monosubstituted phenyl radicals, the substituent can be situated in the 2-position, the 3-position or the 4-position; in disubstituted phenyl radicals, the substituents can be situated in the 2,3-position, 2,4-position, 2,5-position, 2,6-position, 3,4-position or 3,5-position. If a phenyl radical carries a further phenyl radical as a substituent, this phenyl radical in turn can also be unsubstituted or can be substituted by one or two identical or different radicals of the type which are mentioned as substituents on the first phenyl radical, except by a phenyl radical. Naphthyl can be 1-naphthyl or 2-naphthyl.

Heteroaryl is understood as meaning radicals of monocyclic or bicyclic aromatic ring systems, which in the case of the monocyclic systems have a 5-membered ring or a 6-membered ring and in the case of the bicyclic systems have two fused 5-membered rings, a 6-membered ring fused to a 5-membered ring or two fused 6membered rings. They can be conceived as being radicals derived from cyclopentadienyl, phenyl, pentalenyl, indenyl or naphthyl by replacement of one or two CH groups and/or $CH_2$ groups by S, O, N, NH (or N carrying a substituent such as, for example, N—$CH_3$), where the aromatic ring system is retained or an aromatic ring system is formed. In addition to the one or two ring heteroatoms, they contain three to nine ring carbon atoms. Examples of heteroaryl are, in particular, furyl, thienyl, pyrrolyl, imidazolyl, pyrazolyl, 1,3-oxazolyl, 1,2-oxazolyl, 1,3-thiazolyl, 1,2-thiazolyl, pyridyl, pyridazinyl, pyrazinyl, pyrimidyl, indolyl, benzofuranyl, benzothiophenyl, quinolyl, isoquinolyl or benzopyranyl. A heteroaryl radical can be bonded via any suitable carbon atom. For example, a thienyl radical can be present as a 2-thienyl radical or 3-thienyl radical, a furyl radical as a 2-furyl radical or 3-furyl radical, a pyridyl radical as a 2-pyridyl radical, 3-pyridyl radical or 4-pyridyl radical. A radical which is derived from 1,3-thiazole or from imidazole can be bonded via the 2-position, the 4-position or the 5-position. Suitable nitrogen heterocycles can also be present as N-oxides or as quaternary salts having an anion derived from a physiologically tolerable acid as a counterion. Pyridyl radicals can thus be present, for example, as pyridine N-oxides.

The present invention includes all stereoisomeric forms of the compounds of the formula I. Asymmetric centers present in the compounds of the formula I can all independently of one another have the S configuration or the R configuration. The invention includes all possible enantiomers and diastereomers, as well as mixtures of two or more stereoisomeric forms, for example mixtures of enantiomers and/or diastereomers, in all ratios. Enantiomers are thus a subject of the invention in enantiomerically pure form, both as levorotatory and as dextrorotatory antipodes, in the form of racemates and in the form of mixtures of the two enantiomers in all ratios. In the presence of cis/trans isomerism, both the cis form and the trans form and mixtures of these forms in all ratios are a subject of the invention. The preparation of individual stereoisomers can be carried out, if desired, by separation of a mixture according to customary methods, for example by chromatography or crystallization, or by use of stereochemically uniform starting substances in the synthesis or by use of stereoselective reactions. If appropriate, a derivatization can be carried out before separation of stereoisomers. The separation of a stereoisomer mixture can be carried out at the stage of the compounds of the formula I or at the stage of an intermediate in the course of the synthesis. The invention also includes all tautomeric forms of the compounds of the formula I.

Physiologically tolerable salts of the compounds of the formula I are, in particular, nontoxic salts or pharmaceutically utilizable salts. They can contain inorganic or organic salt components (see also Remington's Pharmaceutical Sciences, A. R. Gennaro (Ed.), Mack Publishing Co., 17th Edition, page 1418 (1985)). Such salts can be prepared, for example, from compounds of the formula I and nontoxic inorganic or organic bases, for example, suitable alkali metal compounds or alkaline earth metal compounds, such as sodium hydroxide or potassium hydroxide, or ammonia or organic amino compounds or ammonium hydroxides. Reactions of compounds of the formula I with bases for the preparation of the salts are in general carried out in a solvent or diluent according to customary procedures. On account of the physiological and chemical stability, advantageous salts, in the presence of acidic groups, are in many cases sodium, potassium, magnesium or calcium salts or ammonium salts. Salt formation on the nitrogen atom of the (thio)urea group substituted by the sulfonyl group leads to compounds of the formula II

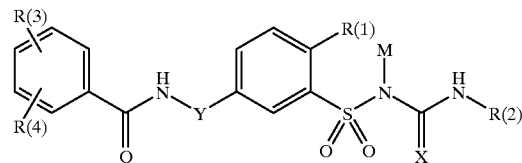

in which R(1), R(2), R(3), R(4), X and Y have the meanings indicated above and the cation M, for example, is an alkali metal ion or an equivalent of an alkaline earth metal ion, for example the sodium, potassium, magnesium or calcium ion, or the unsubstituted ammonium ion or an ammonium ion having one or more organic radicals. An ammonium ion which is M can also be, for example, the cation which is obtained from an amino acid by protonation, in particular the cation obtained from a basic amino acid such as, for example, lysine or arginine.

Compounds of the formula I which contain one or more basic, that is protonatable, groups can be present in the form of their acid addition salts with physiologically tolerable inorganic or organic acids and are used according to the invention, for example as salts with hydrogen chloride, phosphoric acid, sulfuric acid or organic carboxylic acids or sulfonic acids such as, for example, p-toluenesulfonic acid, acetic acid, tartaric acid, benzoic acid, fumaric acid, maleic acid, citric acid etc. If the compounds of the formula I simultaneously contain acidic and basic groups in the molecule, the present invention also includes, in addition to the salt forms described, internal salts or betaines (zwitterions). Acid addition salts can also be obtained from the compounds of the formula I by customary processes known to the person skilled in the art, for example by combination with an organic or inorganic acid in a solvent or dispersant. The present invention also includes all salts of the compounds of the formula I which, because of low physiological tolerability, are not directly suitable for use in pharmaceuticals, but are suitable, for example, as intermediates for chemical reactions or for the preparation of physiologically tolerable salts.

The present invention furthermore includes all solvates of compounds of the formula I, for example hydrates or adducts with alcohols, and also derivatives of the compounds of the formula I such as, for example, esters or amides, and prodrugs and active metabolites.

In the formula I, Y is preferably —$(CH_2)_n$—, particularly preferably —$CH_2$—$CH_2$—.

R(1) is preferably 1. phenyl which is unsubstituted or is substituted by a substituent from the group consisting of halogen, preferably fluorine or chlorine, $(C_1–C_4)$-alkyl, preferably methyl, $(C_1–C_4)$-alkoxy, preferably methoxy, $—S(O)_m—(C_1–C_4)$-alkyl, preferably $—S(O)_m$-methyl, trifluoromethyl and nitro, where the substituent is preferably in the para-position; or
2. monocyclic heteroaryl having one or two identical or different ring heteroatoms, preferably one, from the group consisting of oxygen, sulfur and nitrogen, in particular furyl, thienyl or pyridyl, especially 2-furyl, 2-thienyl, 2-pyridyl or 3-pyridyl; or
3. —S-phenyl; or
4. $(C_2–C_3)$-alkenyl, in particular vinyl or allyl; or
5. ethynyl or 2-phenylethynyl, in particular ethynyl.

R(2) is preferably $(C_1–C_3)$-alkyl, particularly preferably methyl, ethyl or isopropyl.

Preferably, one of the radicals R(3) and R(4) is halogen, in particular chlorine, and the other is $(C_1–C_4)$-alkoxy, in particular $(C_1–C_3)$-alkoxy, especially methoxy.

Furthermore, one of the radicals R(3) and R(4) is preferably in the 2-position and the other in the 5-position of the phenyl ring. Particularly preferably, the benzoyl radical containing the radicals R(3) and R(4) carries a radical R(3), which is $(C_1–C_4)$-alkoxy, in particular $(C_1–C_3)$-alkoxy, especially methoxy, in the 2-position, and a radical R(4), which is halogen, in particular chlorine, in the 5-position.

R(5) is preferably radicals from the group consisting of hydrogen and methyl, particularly preferably hydrogen.

n is preferably 1, 2 or 3, particularly preferably 2.

Preferred compounds of the formula I are those in which one or more of the radicals contained therein have preferred meanings, where all combinations of preferred substituent definitions are a subject of the present invention. The present invention also includes, of all preferred compounds of the formula I, all their stereoisomeric forms and mixtures thereof in all ratios, and their physiologically tolerable salts.

Thus, for example, a group of preferred compounds is formed from those compounds of the formula I in which R(1) is 1. phenyl which is unsubstituted or is substituted by a substituent from the group consisting of halogen, $(C_1–C_4)$-alkyl, $(C_1–C_4)$-alkoxy, $—S(O)_m—(C_1–C_4)$-alkyl, trifluoromethyl and nitro; or
2. monocyclic heteroaryl having one or two identical or different ring heteroatoms from the group consisting of oxygen, sulfur and nitrogen; or
3. —S-phenyl; or
4. $(C_2–C_3)$-alkenyl; or
5. ethynyl or 2-phenylethynyl and all other radicals in the formula I have the meanings indicated in the above definition of the compounds according to the invention, in all their stereoisomeric forms and mixtures thereof in all ratios, and their physiologically tolerable salts.

A further group of preferred compounds is formed, for example, from compounds of the formula Ia

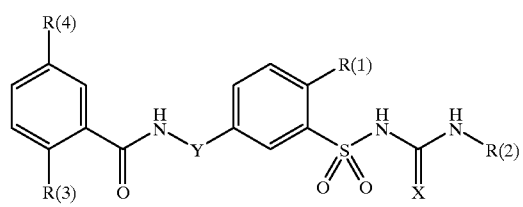

in which
Y is —CH$_2$—CH$_2$—;
R(2) is methyl, ethyl or isopropyl;
R(3) is $(C_1–C_4)$-alkoxy;
R(4) is halogen;
and the radical R(1) in the formula Ia has the meanings indicated in the above definition of the compounds according to the invention, in all their stereoisomeric forms and mixtures thereof in all ratios, and their physiologically tolerable salts.

The present invention also relates to processes for the preparation of the compounds of the formula I, which are explained below and by which the compounds according to the invention are obtainable.

Compounds of the formula I in which X is sulfur, that is 2,5-substituted benzenesulfonylthioureas of the formula Ib

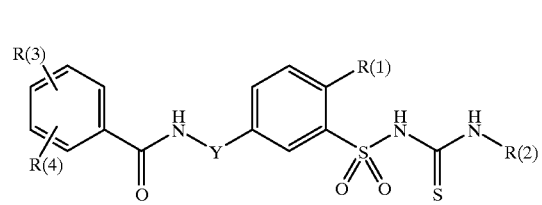

in which R(1), R(2), R(3), R(4) and Y have the abovementioned meanings, can be prepared, for example, by reacting 2,5-substituted benzenesulfonamides of the formula III

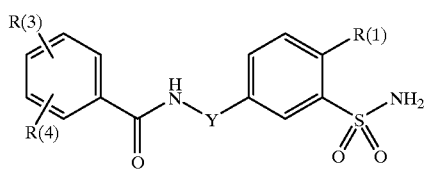

in which R(1), R(3), R(4) and Y have the abovementioned meanings, in an inert solvent or diluent with a base and with an R(2)-substituted isothiocyanate of the formula IV

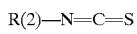

in which R(2) has the meanings indicated above. Suitable bases are, for example, alkali metal or alkaline earth metal hydroxides, hydrides, amides or alkoxides, such as sodium hydroxide, potassium hydroxide, calcium hydroxide, sodium hydride, potassium hydride, calcium hydride, sodium amide, potassium amide, sodium methoxide, sodium ethoxide, potassium tert-butoxide, or quaternary ammonium hydroxides. The reaction of the compound of the formula III with the base can first be carried out in a separate step and the initially resulting salt of the formula V

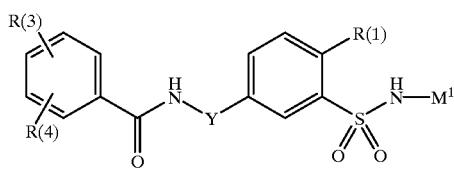

V in which R(1), R(3), R(4) and Y have the abovementioned meanings and $M^1$ is an alkali metal ion, for example sodium or potassium, or an equivalent of an alkaline earth metal ion, for example magnesium or calcium, or an ammonium ion which is inert under the reaction conditions, for example a quaternary ammonium ion, can, if desired, also be intermediately isolated. The salt of the formula V, however, can particularly advantageously also be produced in situ from the compound of the formula III and reacted directly with the isothiocyanate of the formula IV. Suitable inert solvents for the reaction are, for example, ethers such as tetrahydrofuran (THF), dioxane, ethylene glycol dimethyl ether or diethylene glycol dimethyl ether, ketones such as acetone or butanone, nitriles such as acetonitrile, nitro compounds such as nitromethane, esters such as ethyl acetate, amides such as dimethylformamide (DMF) or N-methylpyrrolidone (NMP), hexamethylphosphoramide (HMPT), sulfoxides such as dimethyl sulfoxide (DMSO) or hydrocarbons such as benzene, toluene or xylenes. Mixtures of these solvents with one another are furthermore suitable. The reaction of the compounds of the formula III or V with the compound of the formula IV is in general carried out at temperatures from room temperature to 150° C.

Compounds of the formula I in which X is oxygen, that is 2,5-substituted benzenesulfonylureas of the formula Ic Ic

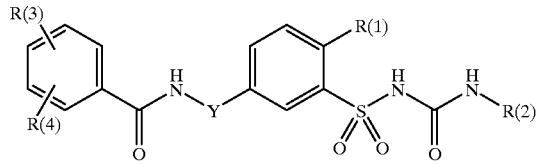

in which R(1), R(2), R(3), R(4) and Y have the abovementioned meanings, can be prepared, for example, by reacting, analogously to the synthesis of the compounds of the formula Ib describe d above, 2,5-substituted benzenesulfonamides of the formula III or their salts of the formula V in an inert solvent or diluent with a base and with an R(2)-substituted isocyanate of the formula VI

R(2)—N=C=O     VI in which R(2) has the meanings indicated above. The above explanations for th e reaction of the isothiocyanates apply to the reaction of the isocyanates correspondingly.

2,5-substituted benzenesulfonylureas of the formula Ic can also be prepared from the 2,5-substituted benzenesulfonamides of the formula III or their salts of the formula V by reaction with R(2)-substituted 2,2,2-trichloroacetamides of the formula VII Cl$_3$C—CO—NH—R(2)     VII in which R(2) has the meanings indicated above, in the presence of a base in an inert, high-boiling solvent such as, for example, DMSO. The compounds of the formula Ic can also be obtained from the urethane derivatives of the 2,5-substituted benzenesulfonamides of the formula VIII, which are accessible from the compounds of the formula III by reaction with chloroformic acid esters, by action of the appropriate amine of the formula R(2)—NH$_2$ in an inert, high-boiling solvent, for example toluene, at temperatures up to the boiling point of the respective solvent (see, for example, J. Med. Chem. 38 (1995) 2357–2377 and bioorg. Med. Chem. 5 (1997) 673–678).

2,5-substituted benzenesulfonylureas of the formula Ic can also be prepared from the corresponding 2,5-substituted benzenesulfonylthioureas of the formula Ib by a conversion reaction (desulfurization). The replacement of the sulfur atom in the thiourea group in the benzenesulfonylthioureas of the formula Ib by an oxygen atom can be carried out, for example, with the aid of oxides or salts of heavy metals or by use of oxidants such as hydrogen peroxide, sodium peroxide or nitrous acid.

2,5-substituted benzenesulfonylureas and -thioureas of the formula I can also be prepared by reaction of amines of the formula R(2)—NH$_2$ with 2,5-substituted benzenesulfonyl isocyanates and isothiocyanates of the formula VIII

VIII

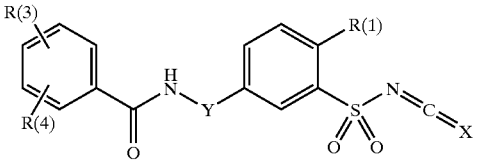

in which R(1), R(3), R(4), X and Y have the abovementioned meanings. The sulfonyl isocyanates of the formula VIII (X=oxygen) can be obtained from the 2,5-substituted benzenesulfonamides of the formula III according to customary methods, for example using phosgene. The sulfonyl isothiocyanates of the formula VIII (X=sulfur) can be prepared by reaction of the sulfonamides of the formula III with alkali metal hydroxides and carbon disulfide in an organic solvent, such as DMF, DMSO or NMP. The di-alkali metal salt of the sulfonyldithiocarbamic acid obtained can be reacted in an inert solvent with a slight excess of phosgene or of a phosgene substitute such as triphosgene or with a chloroformic acid ester (2 equivalents) or with thionyl chloride. The solution of the sulfonyl isothiocyanate thus obtained can be reacted directly with the appropriate substituted amine of the formula R(2)—NH$_2$ or, if compounds of the formula I are to be prepared in which R(2) is hydrogen, with ammonia.

The 2,5-substituted benzenesulfonamides of the formula III, as starting compounds for the process for the synthesis of the 2,5-substituted benzenesulfonyl(thio)ureas of the formula I mentioned, can be prepared by or analogously to known methods, such as are described in the literature, for example in the standard works such as Houben-Weyl, Methoden der Organischen Chemie [Methods of Organic Chemistry], Georg Thieme Verlag, Stuttgart, and Organic Reactions, John Wiley & Sons, Inc., New York, and also in the patent documents indicated above, namely, if appropriate, with suitable adaptation of the reaction conditions, which is familiar to the person skilled in the art. Use can also be made in this case of variants which are known per se, but not mentioned here in greater detail. The starting substances, if desired, can also be formed in situ in such a way that they are not isolated from the reaction mixture, but immediately reacted further.

Thus p-substituted benzene derivatives of the formula IX

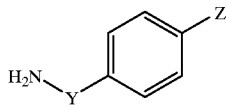

IX in which Y has the abovementioned meaning and Z is bromine or nitro, can be reacted with benzoic acid derivatives to give compounds of the formula X

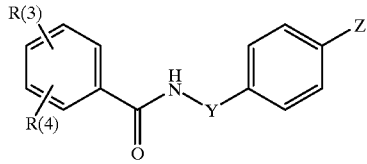

X in which R(3), R(4) and Y have the meanings indicated above and Z is bromine or nitro. In general, this acylation is carried out by first converting the appropriate benzoic acids into reactive derivatives, for example by reaction of the benzoic acid with carbonylbisimidazole in an inert solvent such as, for example, THF, dioxane or DMF, and subsequent reaction with the amine of the formula IX concerned, if appropriate in the presence of a base such as triethylamine or pyridine. Reactive derivatives of the benzoic acids which can be used, for example, are also benzoyl halides or benzoic anhydrides. The reactions are preferably carried out at temperatures from 0° C. up to the boiling point of the chosen solvent, particularly preferably at room temperature. Alternatively, the acylation of the amine of the formula IX with the appropriate benzoic acids can also be carried out, for example, in the presence of condensing agents such as, for example, N,N'-dicyclohexylcarbodiimide or O-((cyano (ethoxycarbonyl)methylene)-amino)-1,1,3,3-tetramethyluronium tetrafluoroborate (TOTU).

Starting from the compounds of the formula X in which Z is nitro, it is possible by means of a reduction of the nitro group using a reductant such as, for example, SnCl$_2$×2 H$_2$O in an inert solvent such as ethyl acetate, diazotization of the resulting amino group and subsequent reaction of the intermediate diazo compound with potassium iodide by processes known per se, such as are described, for example, in Larock, Comprehensive Organic Transformations, VCH, 1989, to obtain the corresponding p-iodo-substituted compounds of the formula XI

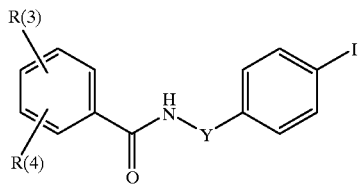

XI in which R(3), R(4) and Y have the meanings indicated above.

The compounds of the formula XI and the compounds of the formula X in which Z is bromine, which together are designated as compounds of the formula XII

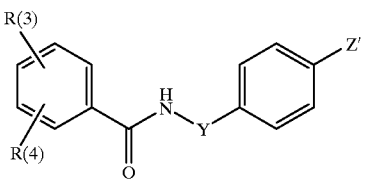

XII in which R(3), R(4) and Y have the meanings indicated above and Z' is bromine or iodine, can be converted in a known manner under suitable reaction conditions into the 2,5-substituted benzenesulfonamides of the formula XIII

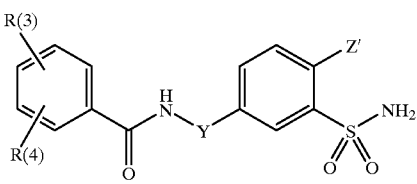

XIII in which R(3), R(4), Y and Z' have the meanings mentioned. The sulfonamides of the formula XIII can be prepared from the compounds of the formula XII in one, two or more steps. In particular, processes are preferred in which the acylamines of the formula XII are first converted into the 2,5-substituted benzenesulfonic acids or their derivatives, such as, for example, the sulfonyl halides, by electrophilic reagents in the presence or absence of inert solvents at temperatures of −20° C. to 120° C., preferably of 0° C. to 100° C. For this, it is possible to carry out, for example, sulfonations with sulfuric acids or oleum, halosulfonations with halosulfonic acids such as chlorosulfonic acid, reactions with sulfuryl halides in the presence of anhydrous metal halides or reactions with thionyl halides in the presence of anhydrous metal halides with subsequent oxidations carried out in a known manner to give sulfonyl chlorides. If sulfonic acids are the primary reaction products, these can either be converted into sulfonyl halides directly in a manner known per se by means of acid halides such as, for example, phosphorus trihalides, phosphorus pentahalides, thionyl halides or oxalyl halides, or after treatment with amines, such as, for example, triethylamine or pyridine, or using alkali metal or alkaline earth metal hydroxides or reagents which form these basic compounds in situ. The sulfonic acid derivatives are converted into the sulfonamides of the formula XIII in a manner known from the literature. Preferably, sulfonyl chlorides are reacted with aqueous ammonia in an inert solvent such as, for example, acetone at temperatures of 0° C. to 100° C.

The sulfonamide group in the compounds of the formula XIII can then be temporarily protected by conversion into the N-(N,N-dimethylaminomethylene)sulfonamide group. The conversion of the compounds of the formula XIII into the dimethylaminomethylene compounds of the formula XIV

XIV

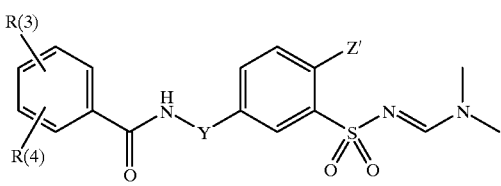

in which R(3), R(4), Y and Z' have the meanings mentioned, can be carried out, for example, by reaction of the compounds of the formula XIII with N,N-dimethylformamide dimethyl acetal (J. Med. Chem. 38 (1995) 2357–2377) or by reaction with N,N-dimethylformamide in the presence of dehydrating agents such as $SOCl_2$, $POCl_3$ or $PCl_5$ (Liebigs Ann. (1995) 1253–1257).

Starting from the compounds of the formula XIV, the compounds of the formula XV

XV

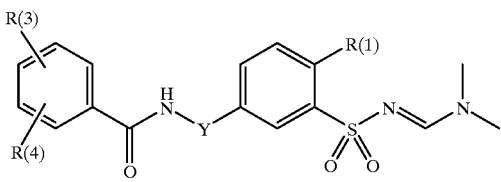

can then be obtained in which R(1), R(3), R(4) and Y are as defined above. The conversion into the compounds of the formula XV can be carried out, for example, by means of palladium-catalyzed Suzuki coupling with arylboronic acids such as phenylboronic acids or heteroarylboronic acids such as thiopheneboronic acids, or by Stille coupling with trialkylstannanes, for example with tributylstannylheteroaromatics such as tributylstannylfuran or trimethylstannylpyridine or with trialkylstannylalkynes or trialkylstannylalkenes such as ethynyltributylstannane. The Suzuki coupling is preferably carried out with the aryl bromides (compounds of the formula XIV where Z'=Br) with palladium(II) acetate and triphenylphosphine or tetrakis(triphenylphosphine)palladium as a catalyst in the presence of a base such as, for example, cesium carbonate or potassium carbonate (see, for example, Synthetic Commun. 11 (1981) 513; J. Med. Chem. 38 (1995) 2357–2377; Liebigs Ann. (1995) 1253–1257). The Stille coupling is preferably carried out with the aryl iodides (compounds of the formula XIV where Z'=I) using bis(triphenylphosphine)palladium (II) chloride as a catalyst (see, for example, Tetrahedron Lett. (1986) 4407–4410). The preparation of suitable stannanes is described, for example, in Tetrahedron 49 (1993) 3325–3342.

Compounds of the formula XV in which R(1) is phenylsulfanyl can be prepared by copper(I) iodide-catalyzed nucleophilic substitution of the aryl iodides of the formula XIV (Z'=I) with sodium thiophenolate (see, for example, Chem. Lett. (1980) 1363–1364). The thioether group —S— thus introduced, and also a thioether group in another position of the molecule of the formula I, can be oxidized to the sulfoxide group —S(O)— or to the sulfone group —$S(O)_2$— by standard processes, for example using a peracid such as m-chloroperbenzoic acid or monoperoxyphthalic acid.

The subsequent removal of the dimethylaminomethylene group functioning as a sulfonamide protective group from the compounds of the formula XV then leads to the desired compounds of the formula III. This removal can be carried out either under basic or acidic conditions. Preferably, it is carried out by treatment of the compounds of the formula XV in a suitable solvent, for example an alcohol, with acids such as, for example, hydrochloric acid.

The compounds of the formula I influence the action potential of cells, in particular of cardiac muscle cells. In particular, they have a normalizing effect on a disturbed action potential, such as is present, for example, in ischemias, and are suitable, for example, for the treatment and prophylaxis of disorders of the cardiovascular system, in particular of arrhythmias and their sequelae. The efficacy of the compounds of the formula I can be demonstrated, for example, in the model described boiow, in which the duration of the action potential is determined on the papillary muscle of the guinea pig.

The compounds of the formula I and their physiologically tolerable salts can therefore be used as pharmaceuticals on their own, in mixtures with one another or in the form of pharmaceutical preparations in animals, preferably in mammals, and in particular in humans. Mammals on which the compounds of the formula I can be used or tested are, for example, monkeys, dogs, mice, rats, rabbits, guinea pigs, cats and larger farm animals such as, for example, cattle and pigs. The invention therefore also relates to the compounds of the formula I and their physiologically tolerable salts for use as pharmaceuticals, and to pharmaceutical preparations (or pharmaceutical compositions) which contain an efficacious dose of at least one compound of the formula I and/or a physiologically tolerable salt thereof as an active constituent and a customary, pharmaceutically tolerable carrier. The pharmaceutical preparations can be intended for enteral or parenteral use and normally contain 0.5 to 90 percent by weight of the compound of the formula I and/or its physiologically tolerable salts. The amount of active compound of the formula I and/or its physiologically tolerable salts in the pharmaceutical preparations is in general approximately 0.2 to approximately 500 mg, preferably approximately 1 to approximately 200 mg.

The pharmaceutical preparations according to the invention can be produced in a manner known per se. For this, the compounds of the formula I and/or their physiologically tolerable salts are mixed together with one or more solid or liquid vehicles and/or excipients and, if desired, in combination with other pharmaceuticals, for example cardiovascular-active pharmaceuticals such as, for example, calcium antagonists or ACE inhibitors, and brought into a suitable dose form and administration form, which can then be used as a pharmaceutical in human medicine or veterinary medicine.

Suitable vehicles are organic and inorganic substances which are suitable, for example, for enteral (for example oral or rectal) administration or for parenteral administration (for example intravenous, intramuscular or subcutaneous injection or infusion) or for topical or percutaneous application and do not react with the compounds of the formula I in an undesired manner, for example water, vegetable oils, waxes, alcohols such as ethanol, propanediol or benzyl alcohols, glycerol, polyols, polyethylene glycols, polypropylene glycols, glycerol triacetate, gelatin, carbohydrates such as lactose or starch, stearic acid and its salts such as magnesium stearate, talc, lanolin and petroleum jelly. In particular, pharmaceutical forms such as tablets, sugar-coated tablets, capsules, suppositories, solutions, preferably oily or aqueous solutions, syrups, juices or drops, furthermore suspensions or emulsions, are used for oral and rectal administration.

Ointments, creams, pastes, lotions, gels, sprays, foams, aerosols, solutions or powders, in particular, are used for topical administration. Solvents for solutions which can be used are, for example, water or alcohols such as ethanol, isopropanol or 1,2-propanediol or their mixtures with one another or with water. Further possible pharmaceutical forms are, for example, also implants. The compounds of the formula I can also be lyophilized and the lyophilizates obtained used, for example, for the production of injection preparations. Liposomal preparations are also possible, in particular for topical application. The pharmaceutical preparations can contain excipients (or additives), such as, for example, lubricants, preservatives, thickeners, stabilizing agents, wetting agents, agents for achieving a depot effect, emulsifiers, salts (for example for affecting the osmotic pressure), buffer substances, colorants, flavorings and/or aromatizers. The pharmaceutical preparations, if desired, can also contain one or more further active compounds and/or, for example, one or more vitamins.

The compounds of the formula I and their physiologically tolerable salts are valuable therapeutics, which are suitable for use in humans and animals not only as antiarrhythmics and for the control and prevention of the sequelae of arrhythmias, but also for treatment and prophylaxis in other disorders of the cardiovascular system, for example cardiac insufficiency, ischemias or heart transplantation, or in cerebral vascular disorders. In particular, they are used as antiarrhythmics for the treatment of cardiac arrhythmias of very different origins and especially for the prevention of sudden heart death due to arrhythmia. Examples of arrhythmic disorders of the heart are supraventricular arrhythmias such as, for example, atrial tachycardia, atrial flutters or paroxysomal supraventricular arrhythmias, or ventricular arrhythmias such as ventricular extrasystoles, but in particular life-threatening ventricular tachycardia or the particularly dangerous ventricular fibrillation. They are particularly suitable for those cases where arrhythmias are a result of a constriction of a coronary vessel, such as occur, for example, in angina pectoris or during acute cardiac infarct or as a chronic result of a cardiac infarct. They are therefore particularly suitable in postinfarct patients for the prevention of sudden heart death. Further syndromes in which arrhythmias of this type and/or sudden heart death due to arrhythmia play a role are, for example, cardiac insufficiency or cardiac hypertrophy as a result of chronically raised blood pressure.

Moreover, the compounds of the formula I are able to positively affect decreased contractility of the heart and a weakened myocardial contractile force. This can be a disease-related decline in cardiac contractility, such as, for example, in cardiac insufficiency, but also acute cases such as heart failure in the case of the effect of shock. Likewise, under the influence of the compounds of the formula I in a heart transplantation, the heart can also resume its capability faster and more reliably after the operation has taken place. The same applies to operations on the heart which necessitate temporarily stopping cardiac activity by means of cardioplegic solutions.

The present invention therefore also relates to the use of the compounds of the formula I and/or their physiologically tolerable salts for the treatment and prophylaxis of the syndromes mentioned, their use for the production of pharmaceuticals for use in the syndromes mentioned and methods for the treatment and prophylaxis of the syndromes mentioned.

The dosage of the compounds of the formula I or their physiologically tolerable salts depends, as is customary, on the circumstances of the respective individual case and is adjusted to this by the person skilled in the art according to the customary rules and procedures. It thus depends, on the compound of the formula I administered, on the nature and severity of the individual syndrome, on the condition of the individual patient or on whether treatment is acute or prophylactic. Normally, in the case of administration to an adult weighing about 75 kg, a dose is needed which is at least approximately 0.01 mg, in particular at least approximately 0.1 mg, especially at least approximately 1 mg, and which at most is approximately 100 mg, in particular at most approximately 10 mg (all data in each case in mg per kg of body weight per day). In general, a dose range from approximately 1 mg to approximately 10 mg per kg of body weight per day is particularly suitable. The dose can be administered in the form of an oral or parenteral individual dose or can be divided into two or more, for example two, three or four, individual doses. If acute cases of cardiac arrhythmias are treated, for example in an intensive care unit, parenteral administration, for example by injection or infusion, can be advantageous. A preferred dose range in critical situations can then be approximately 1 mg to 100 mg per kg of body weight per day and can be administered, for example, as an intravenous continuous infusion. If appropriate, depending on individual behavior, it may be necessary to deviate upward or downward from the doses indicated.

The compounds of the formula I inhibit ATP-sensitive potassium channels of cells and, apart from as a pharmaceutical active compound in human medicine and veterinary medicine, can also be employed as an aid for biochemical investigations or as a scientific tool if appropriate influencing of ion channels is intended, or for the isolation of potassium channels. They can also be used for diagnostic purposes, for example in in-vitro diagnoses of cell samples or tissue samples. The compounds of the formula I and their salts can furthermore be used as intermediates for the preparation of further pharmaceutical active compounds.

The invention is illustrated by the examples below, without being restricted to these.

EXAMPLE

Abbreviations

| | |
|---|---|
| DCI | desorption chemical ionization |
| DCM | dichloromethane |
| DMF | N,N-dimethylformamide |
| EA | ethyl acetate |
| ESI | electron spray ionization |
| FAB | fast atom bombardment |
| M.p. | melting point |
| h | hour(s) |
| min. | minute(s) |
| MS | mass spectrum |
| THF | tetrahydrofuran |

Example 1

5-(2-(5-Chloro-2-methoxybenzamido)ethyl)-N-(methylaminothiocarbonyl)-2-phenylbenzenesulfonamide

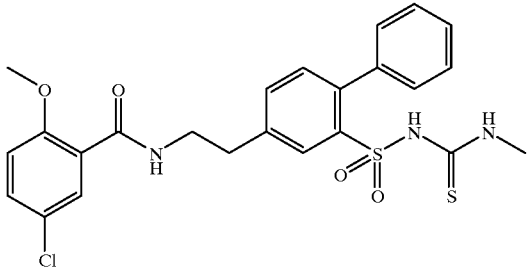

a) N-(2-(4-Bromophenyl)ethyl)-5-chloro-2-methoxybenzamide

A solution of 8.3 g (44.4 mmol) of 5-chloro-2-methoxybenzoic acid and 7.8 g (48.1 mmol) of carbonylbisimidazole in 200 ml of absolute THF was stirred at room temperature for 2 h. 7.7 ml (50.0 mmol) of 2-(4-bromophenyl)ethylamine and 10 ml of triethylamine were added and the resulting solution was stirred at room temperature for 24 h. The reaction solution was then poured onto water, and the deposited precipitate was filtered off with suction and washed with water. Drying of the precipitate yielded 15.8 g of the title compound in the form of a slightly yellow-colored solid. M.p.: 104–109° C. $R_f$ (silica gel, EA/heptane 2:1)=0.66. MS (ESI): m/z=368/370 (M+H)$^+$.

b) 2-Bromo-5-(2-(5-chloro-2-methoxybenzamido)ethyl)benzenesulfonamide 6.2 g (16.9 mmol) of the compound of Example 1a) were introduced in portions into 55 ml of chlorosulfonic acid and the resulting solution was stirred at 50° C. for 6 h. The reaction solution was then added dropwise to 400 ml of ice and the deposited precipitate was filtered off with suction. The precipitate was stirred in 160 ml of acetone and 32 ml of conc. ammonia, the acetone was stripped off on a rotary evaporator and the pH of the remaining solution was adjusted to 5 by addition of 2N hydrochloric acid. It was then extracted a number of times with DCM and the combined DCM extracts were dried over sodium sulfate and concentrated. The resulting crystalline residue was washed with water and a little methanol and dried in a high vacuum. 3.9 g of the title compound resulted in the form of a beige solid. M.p.: 190° C. $R_f$ (silica gel, EA/heptane 2:1)=0.36. MS (DCI): m/z=447/449 (M+H)$^+$.

c) 2-Bromo-5-(2-(5-chloro-2-methoxybenzamido)ethyl)-N-(dimethylaminomethylene)benzenesulfonamide 2.9 g (6.5 mmol) of the compound of Example 1b) were dissolved in 20 ml of absolute DMF, 7.7 mmol of dimethylformamide dimethyl acetal were added and the resulting solution was stirred at room temperature for 30 min. It was concentrated to dryness and the residue obtained was stirred with 30 ml of water and 30 ml of 5% strength NaHSO$_4$ solution. The residue which remained was filtered off with suction and taken up in DCM. Drying of the DCM solution over sodium sulfate and stripping off the solvent in vacuo afforded a brown oil, which was purified by chromatography on silica gel using EA/toluene (10:1) as eluent. Combination and concentration of the product-containing fractions finally yielded 2.6 g of the title compound as a white solid. M.p.:150–152° C. $R_f$ (silica gel, EA/heptane 5:1)=0.31. MS (DCI): m/z=502/504 (M+H)$^+$.

d) 5-(2-(5-Chloro-2-methoxybenzamido)ethyl)-N-(dimethylaminomethylene)-2-phenylbenzenesulfonamide A solution of 244 mg (2.0 mmol) of benzeneboronic acid in 10 ml of ethanol was added dropwise to a suspension of 1.0 g (2.0 mmol) of the compound of Example 1c) and 71 mg (0.02 mmol) of tetrakis(triphenylphosphine)palladium in 10 ml of toluene. 2.3 ml of a 2 M Cs$_2$CO$_3$ solution were added and the reaction solution was stirred at reflux (80° C.) for 4 h. It was then concentrated to dryness, the resulting residue was taken up in DCM/water and the organic phase was separated. The separated organic phase was washed twice with water, dried over sodium sulfate and concentrated. Purification of the residue by chromatography on silica gel using EA/toluene (8:1) as eluent yielded 684 mg of the title compound in the form of an amorphous foam. $R_f$ (silica gel, DCM/methanol 20:1)=0.40. MS (DCI): m/z=500 (M+H)$^+$.

e) 5-(2-(5-Chloro-2-methoxybenzamido)ethyl)-2-phenylbenzenesulfonamide

A solution of 464 mg (0.93 mmol) of the compound of Example 1d) in 9 ml of methanol and 2.4 ml of conc. hydrochloric acid was stirred under reflux for 5 h. Methanol was then stripped off in vacuo and the pH of the residual aqueous solution was adjusted to 4 by addition of 6N sodium hydroxide solution. It was extracted with EA, and the combined extracts were washed with water, dried over sodium sulfate and concentrated. Chromatographic purification of the resulting residue on silica gel using EA/toluene (10:1) as eluent yielded 325 mg of the title compound as a slightly yellow-colored solid. M.p.: 134–136° C. $R_f$ (silica gel, EA/heptane 5:1)=0.73. MS (FAB): m/z=445 (M+H)$^+$.

f) 5-(2-(5-Chloro-2-methoxybenzamido)ethyl)-N-(methylaminothiocarbonyl)-2-phenylbenzenesulfonamide A solution of 188 mg (0.42 mmol) of the compound of Example 1e) and 56 mg (0.50 mmol) of potassium tert-butoxide in 2.5 ml of absolute DMF was stirred under an argon atmosphere for 15 min. 465 μl (0.46 mmol) of a 1 M solution of methyl isothiocyanate in DMF were then added dropwise and the resulting solution was stirred at 80° C. for 1 h. The reaction solution was then added dropwise to 30 ml of 1 N hydrochloric acid and the deposited precipitate was filtered off with suction. The precipitate was dissolved in DCM/EA, and the solution was dried over sodium sulfate and concentrated. The residue was triturated with a little EA and the residual precipitate was filtered off with suction. Drying of the precipitate in a high vacuum yielded 163 mg of the title compound as a white solid. M.p.: 192–196° C. $R_f$ (silica gel, EA/heptane 5:1)=0.43. MS (DCI): m/z=518 (M+H)$^+$

Example 2

5-(2-(5-Chloro-2-methoxybenzamido)ethyl)-N-(methylaminocarbonyl)-2-phenylbenzenesulfonamide

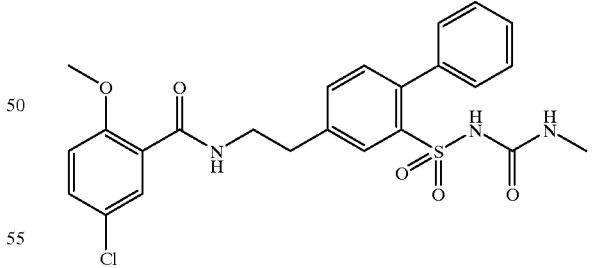

96 mg (0.19 mmol) of the compound of Example 1f) were dissolved in 1 ml of 1 N sodium hydroxide solution. 80 μl of 35% strength H$_2$O$_2$ solution were added and the reaction solution was heated on a water bath for 25 min. The pH of the solution was then adjusted to 2 by addition of 1N hydrochloric acid, and the deposited precipitate was filtered off with suction, washed with a little water and finally dried in a high vacuum. 83 mg of the title compound resulted as a white solid. $R_f$ (silica gel, EA/heptane 5:1)=0.26. MS (DCI): m/z=502 (M+H)$^+$.

Example 3

5-(2-(5-Chloro-2-methoxybenzamido)ethyl)-N-(ethylaminothiocarbonyl)-2-phenylbenzenesulfonamide

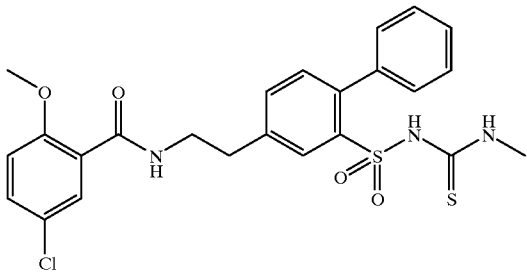

The preparation was carried out according to the process mentioned in Example 1f), ethyl isothiocyanate being used instead of methyl isothiocyanate. Starting from 159 mg (0.36 mmol) of the compound of Example 1e) and 36 µl (0.39 mmol) of ethyl isothiocyanate, after chromatography on silica gel using EA/methanol (80:1) as eluent 123 mg of the title compound resulted in the form of a white solid. M.p.: 168–170° C. $R_f$ (silica gel, EA/methanol 40:1)=0.64. MS (FAB): m/z=532 (M+H)$^+$.

Example 4

5-(2-(5-Chloro-2-methoxybenzamido)ethyl)-N-(ethylaminocarbonyl)-2-phenylbenzenesulfonamide

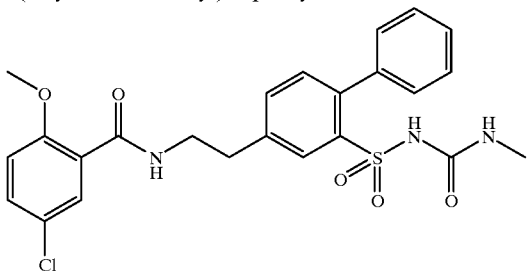

The preparation was carried out according to the process mentioned in Example 2). Starting from 70 mg (0.13 mmol) of the compound of Example 3), 54 mg of the title compound resulted in the form of a white amorphous solid. $R_f$ (silica gel, EA/heptane 10:1)=0.41. MS (FAB): m/z=516 (M+H)$^+$.

Example 5

5-(2-(5-Chloro-2-methoxybenzamido)ethyl)-N-(isopropylaminothiocarbonyl)-2-phenylbenzenesulfonamide

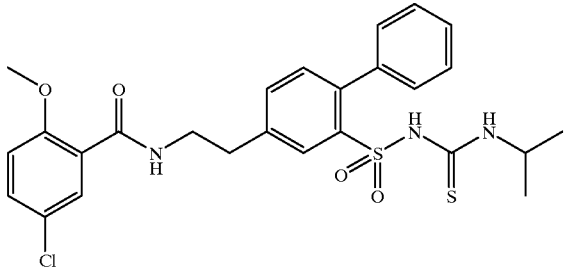

The preparation was carried out according to the process mentioned in Example 1f), isopropyl isothiocyanate being used instead of methyl isothiocyanate. Starting from 162 mg (0.36 mmol) of the compound of Example 1e) and 42 µl (0.40 mmol) of isopropyl isothiocyanate, after chromatography on silica gel using EA/heptane (10:1) as eluent 110 mg of the title compound resulted in the form of a slightly yellow-colored, amorphous solid. $R_f$ (silica gel, EA)=0.62. MS (FAB): m/z=546 (M+H)$^+$.

Example 6

5-(2-(5-Chloro-2-methoxybenzamido)ethyl)-N-(isopropylaminocarbonyl)-2-phenylbenzenesulfonamide

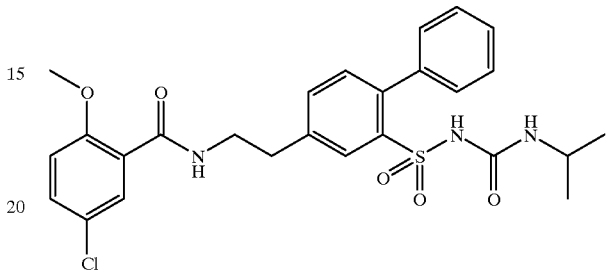

The preparation was carried out according to the process mentioned in Example 2). Starting from 70 mg (0.13 mmol) of the compound of Example 5), 52 mg of the title compound resulted in the form of a white amorphous solid. $R_f$ (silica gel, EA)=0.63. MS (FAB): m/z=530 (M+H)$^+$.

Example 7

5-(2-(5-Chloro-2-methoxybenzamido)ethyl)-2-(4-fluorophenyl)-N-(methyl-aminothiocarbonyl)benzenesulfonamide

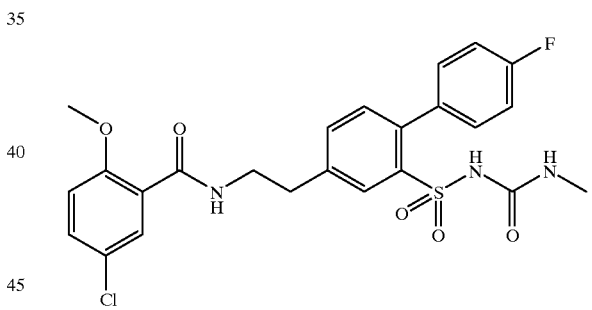

a) 5-(2-(5-Chloro-2-methoxybenzamido)ethyl)-N-(dimethylamino-methylene)-2-(4-fluorophenyl)benzenesulfonamide The preparation was carried out by reaction of the compound of Example 1c) and 4-fluorobenzeneboronic acid according to the process mentioned in Example 1d). Starting from 1.0 g (2.0 mmol) of the compound of Example 1c) and 280 mg (2.0 mmol) of 4-fluorobenzeneboronic acid, after chromatography on silica gel using EA/toluene (5:1) as eluent, 229 mg of the title compound resulted as a slightly yellow-colored, amorphous solid. $R_f$ (silica gel, EA/toluene 5:1)=0.53. MS (DCI): m/z=518 (M+H)$^+$.

b) 5-(2-(5-Chloro-2-methoxybenzamido)ethyl)-2-(4-fluorophenyl)benzenesulfonamide The preparation was carried out from the compound of Example 7a) according to the process mentioned in Example 1e). Starting from 222 mg (0.43 mmol) of the compound of Example 7b), 183 mg of the title compound resulted as a slightly yellow-colored solid. M.p.: 195° C. $R_f$ (silica gel, EA/heptane 10:1)=0.88. MS (DCI): m/z=463 (M+H)$^+$.

c) 5-(2-(5-Chloro-2-methoxybenzamido)ethyl)-2-(4-fluorophenyl)-N-(methyl-aminothiocarbonyl)benzenesulfonamide The preparation was carried out by reaction of the compound of Example 7b) and methyl isothiocyanate according to the process mentioned in Example 1f). Starting from 178 mg (0.39 mmol) of the compound of Example 7b) and 423 μl (0.42 mmol) of methyl isothiocyanate solution, 160 mg of the title compound were obtained as a white solid. M.p.: 181–186° C. $R_f$ (silica gel, EA/heptane 10:1)=0.63. MS (DCI): m/z=537 (M+H)$^+$.

Example 8

5-(2-(5-Chloro-2-methoxybenzamido)ethyl)-2-(4-chlorophenyl)-N-(methyl-aminothiocarbonyl)benzenesulfonamide

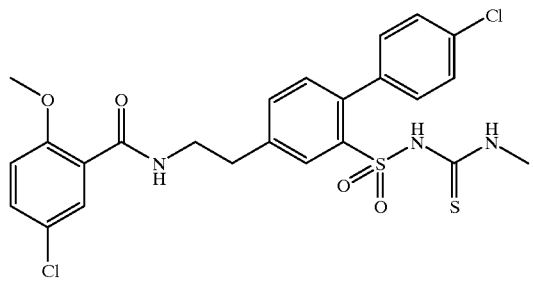

a) 5-(2-(5-Chloro-2-methoxybenzamido)ethyl)-2-(4-chlorophenyl)-N-(dimethylaminomethylene)benzenesulfonamide The preparation was carried out by reaction of the compound of Example 1c) and 4-chlorobenzeneboronic acid according to the process mentioned in Example 1d). Starting from 1.0 g (2.0 mmol) of the compound of Example 1c) and 311 mg (2.0 mmol) of 4-chlorobenzeneboronic acid, after chromatography on silica gel using EA/toluene (5:1) as eluent 382 mg of the title compound resulted as a slightly yellow-colored, solid foam. $R_f$ (silica gel, EA/toluene 5:1)=0.58. MS (DCI): m/z=534 (M+H)$^+$.

b) 5-(2-(5-Chloro-2-methoxybenzamido)ethyl)-2-(4-chlorophenyl)benzenesulfonamide The preparation was carried out from the compound of Example 8a) according to the process mentioned in Example 1e). Starting from 376 mg (0.71 mmol) of the compound of Example 8a), 295 mg of the title compound resulted as a slightly yellow-colored solid. M.p.: 185° C. $R_f$ (silica gel, EA/heptane 5:1)=0.72. MS (DCI): m/z=479 (M+H)$^+$.

c) 5-(2-(5-Chloro-2-methoxybenzamido)ethyl)-2-(4-chlorophenyl)-N-(methylaminothiocarbonyl)benzenesulfonamide The preparation was carried out by reaction of the compound of Example 8b) and methyl isothiocyanate according to the process mentioned in Example 1f). Starting from 180 mg (0.38 mmol) of the compound of Example 8b) and 413 μl (0.41 mmol) of methyl isothiocyanate solution, 150 mg of the title compound were obtained as a white solid. M.p.: 189–192° C. $R_f$ (silica gel, EA/heptane 5:1)=0.53. MS (FAB): m/z=552 (M+H)$^+$.

Example 9

5-(2-(5-Chloro-2-methoxybenzamido)ethyl)-2-(4-methoxyphenyl)-N-ethylaminothiocarbonyl)benzenesulfonamide

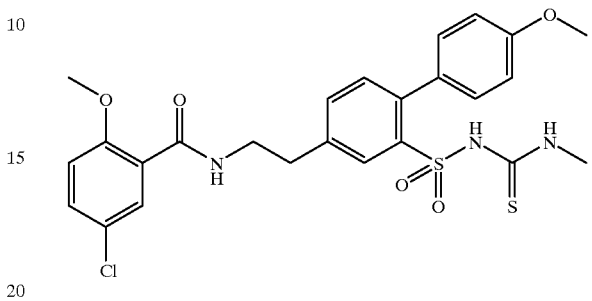

a) 5-(2-(5-Chloro-2-methoxybenzamido)ethyl)-N-(dimethylaminomethylene)-2-(4-methoxyphenyl)benzenesulfonamide The preparation was carried out by reaction of the compound of Example 1c) and 4-methoxybenzeneboronic acid according to the process mentioned in Example 1d). Starting from 638 mg (1.27 mmol) of the compound of Example 1c) and 193 mg (1.27 mmol) of 4-methoxybenzeneboronic acid, after chromatography on silica gel using EA/toluene (20:1) as eluent 249 mg of the title compound resulted as a slightly yellow-colored, amorphous solid. $R_f$ (silica gel, EA/toluene 8:1)=0.38. MS (DCI): m/z=530 (M+H)$^+$.

b) 5-(2-(5-Chloro-2-methoxybenzamido)ethyl)-2-(4-methoxyphenyl)-benzenesulfonamide The preparation was carried out from the compound of Example 9a) according to the process mentioned in Example 1e). Starting from 249 mg (0.47 mmol) of the compound of Example 9a), 165 mg of the title compound resulted as a beige solid. M.p.: 205–208° C. $R_f$ (silica gel, EA/heptane 8:1)=0.70. MS (DCI): m/z=475 (M+H)$^+$.

c) 5-(2-(5-Chloro-2-methoxybenzamido)ethyl)-2-(4-methoxyphenyl)-N-(methylaminothiocarbonyl)benzenesulfonamide The preparation was carried out by reaction of the compound of Example 9b) and methyl isothiocyanate according to the process mentioned in Example 1f). Starting from 159 mg (0.34 mmol) of the compound of Example 9b) and 368 μl (0.37 mmol) of methyl isothiocyanate solution, 142 mg of the title compound were obtained as a white solid. M.p.: 185–188° C. $R_f$ (silica gel, EA/heptane 5:1)=0.36. MS (FAB): m/z=548 (M+H)$^+$.

Example 10

5-(2-(5-Chloro-2-methoxybenzamido)ethyl)-N-(ethylaminothiocarbonyl)-2-(4-methylthiophenyl)benzenesulfonamide

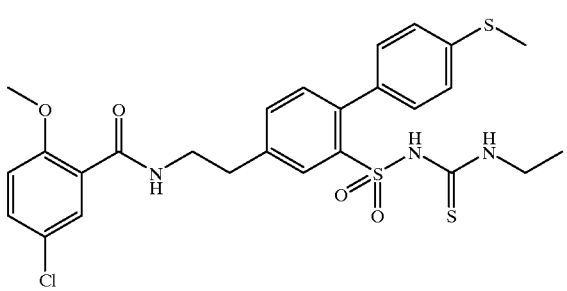

a) 5-(2-(5-Chloro-2-methoxybenzamido)ethyl)-N-(dimethylamino-methylene)-2-(4-methylthiophenyl)benzenesulfonamride The preparation was carried out by reaction of the compound of Example 1c) and 4-methylthiobenzeneboronic acid according to the process mentioned in Example 1d). Starting from 5.0 g (9.95 mmol) of the compound of Example 1c) and 1.67 9 (9.95 mmol) of 4-methylthiobenzeneboronic acid, after chromatography on silica gel using EA/toluene (5:1) as eluent 3.17 g of the title compound resulted as a white, amorphous foam. $R_f$ (silica gel, EA/toluene 5:1)= 0.42. MS (DCI): m/z=546 (M+H)$^+$.

b) 5-(2-(5-Chloro-2-methoxybenzamido)ethyl)-2-(4-methylthiophenyl)-benzenesulfonamide The preparation was carried out from the compound of Example 10a) according to the process mentioned in Example 1e). Starting from 1.0 g (1.83 mmol) of the compound of Example 10a), 634 mg of the title compound resulted as a beige solid. M.p.: 165–168° C. $R_f$ (silica gel, EA/heptane 5:1)=0.69. MS (DCI): m/z=491 (M+H)$^+$.

c) 5-(2-(5-Chloro-2-methoxybenzamido)ethyl)-N-(ethylaminothiocarbonyl)-2-(4-methylthiophenyl)benzenesulfonamide The preparation was carried out by reaction of the compound of Example 10b) and ethyl isothiocyanate according to the process mentioned in Example 1f). Starting from 225 mg (0.46 mmol) of the compound of Example 10b) and 46 µl (0.50 mmol) of ethyl isothiocyanate, 205 mg of the title compound were obtained as a white solid. M.p.: 178–179° C. $R_f$(silica gel, EA/heptane 5:1)=0.62. MS (DCI): m/z=578 (M+H)$^+$.

Example 11

5-(2-(5-Chloro-2-methoxybenzamido)ethyl)-N-(methylaminothiocarbonyl)-2-4-methylsulfonylphenyl)benzenesulfonamide

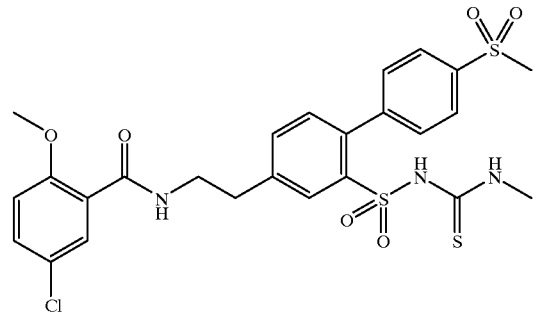

a) 5-(2-(5-Chloro-2-methoxybenzamido)ethyl)-N-(dimethylaminomethylene)-2-(4-methylsulfonylphenyl)benzenesulfonamide A solution of 1.15 g (2.10 mmol) of the compound of Example 10a) and 1.0 g (4.21 mmol) of 3-chloroperoxybenzoic acid in 60 ml of DCM was stirred at room temperature for 2 h. The reaction solution was then treated with 115 ml of 10% strength sodium bisulfite solution, the organic phase was separated off and the aqueous phase was extracted with EA. The combined organic phases were dried over sodium sulfate and concentrated, and the resulting residue was purified by chromatography on silica gel using EA/toluene (5:1). 1.35 g of the title compound were obtained as a white, amorphous foam. $R_f$ (silica gel, EA)=0.40. MS (DCI): m/z=578 (M+H)$^+$.

b) 5-(2-(5-Chloro-2-methoxybenzamido)ethyl)-2-(4-methylsulfonylphenyl)-benzenesulfonamide The preparation was carried out from the compound of Example 11a) according to the process mentioned in Example 1e). Starting from 1.35 g (2.34 mmol) of the compound of Example 11a), 1.11 g of the title compound resulted in the form of a white solid. M.p.: 114° C. $R_f$(silica gel, EA)=0.62. MS (DCI): m/z=523 (M+H)$^+$.

c) 5-(2-(5-Chloro-2-methoxybenzamido)ethyl)-N-(methylaminothiocarbonyl)-2-(4-methylsulfonylphenyl)benzenesulfonamide The preparation was carried out from the compound of Example 11b) according to the process mentioned in Example 1f). Starting from 150 mg (0.29 mmol) of the compound of Example 11b), after chromatographic purification on silica gel using EA as eluent 107 mg of the title compound resulted as a white, amorphous solid. $R_f$ (silica gel, EA)=0.19. MS (FAB): m/z=596 (M+H)$^+$.

Example 12

5-(2-(5-Chloro-2-methoxybenzamido)ethyl)-N-(methylaminothiocarbonyl)-2-(2-thienyl)benzenesulfonamide

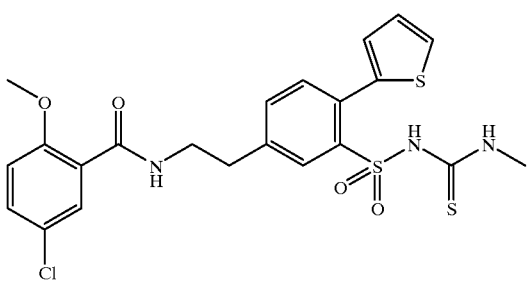

a) 5-(2-(5-Chloro-2-methoxybenzamido)ethyl )-N-(dimethylaminomethylene)-2-(2thienyl)benzenesulfonamide The preparation was carried out by reaction of the compound of Example 1c) with 2-thiopheneboronic acid according to the process mentioned in Example 1d). Starting from 3.0 g (5.97 mmol) of the compound of Example 1c) and 766 mg (5.97 mmol) of 2-thiopheneboronic acid, after chromatographic purification on silica gel using EA/toluene (8:1) as eluent 580 mg of the title compound resulted as an amorphous solid. $R_f$ (silica gel, EA/toluene 8:1)=0.37. MS (FAB): m/z=506 (M+H)$^+$.

b) 5-(2-(5-Chloro-2-methoxybenzamido)ethyl)-2-(2-thienyl)benzenesulfonamide

The preparation was carried out from the compound of Example 12a) according to the process mentioned in Example 1e). Starting from 500 mg (0.99 mmol) of the compound of Example 12a), 282 mg of the title compound resulted as a pale yellow, amorphous foam. $R_f$ (silica gel, EA/toluene 8:1)=0.78. MS (FAB): m/z=451 (M+H)$^+$.

c) 5-(2-(5-Chloro-2-methoxybenzamido)ethyl)-N-(methylaminothiocarbonyl)-2-(2-thienyl)benzenesulfonamide The preparation was carried out from the compound of Example 12b) according to the process mentioned in Example 1f). Starting from 161 mg (0.36 mmol) of the compound of Example 12b), after chromatographic purification on silica gel using EA/methanol (40:1) as eluent 141 mg of the title compound resulted as pale yellow solid. M.p.: 189–191° C. $R_f$ (silica gel, EA/heptane 10:1)=0.27. MS (FAB): m/z=524 (M+H)$^+$.

Example 13

5-(2-(5-Chloro-2-methoxybenzamido)ethyl)-N-(methylaminocarbonyl)-2-(2-thienyl)benzenesulfonamide

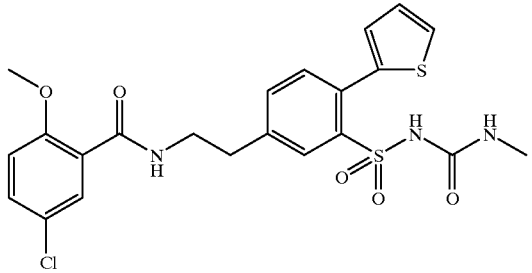

The preparation was carried out from the compound of Example 12c) according to the process mentioned in Example 2). Starting from 70 mg (0.13 mmol) of the compound of Example 12c), 61 mg of the title compound were obtained as a white, amorphous solid. $R_f$ (silica gel, EA/heptane 10:1)=0.23. MS (DCI): m/z=508 (M+H)$^+$.

Example 14

5-(2-(5-Chloro-2-methoxybenzamido)ethyl)-2-(2-furyl)-N-(methylaminothiocarbonyl)benzenesulfonamide

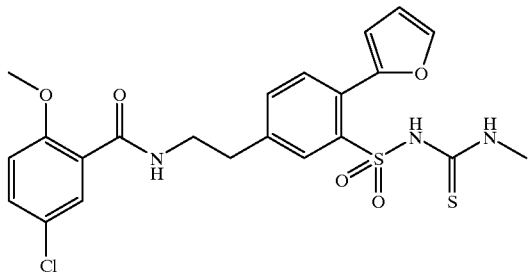

a) 5-Chloro-2-methoxy-N-(2-(4-nitrophenyl)ethyl)benzamide

A solution of 8.8 g (47.2 mmol) of 5-chloro-2-methoxybenzoic acid and 8.5 g (51.9 mmol) of carbonylbisimidazole in 180 ml of absolute THF was stirred at room temperature for 2 h. 10 g (49.7 mmol) of 2-(4-nitrophenyl)ethylamine hydrochloride and 9.4 ml of triethylamine were added and the resulting solution was then stirred overnight at room temperature. The reaction solution was then slowly poured onto 1.2 l of 1N hydrochloric acid, and the deposited precipitate was filtered off and washed with water. Drying of the precipitate in a high vacuum yielded 13.8 g of the title compound as a white solid. M.p.: 159–160° C. $R_f$ (silica gel, EA/heptane 4:1)=0.46. MS (ESI): m/z=334 (M+H)$^+$.

b) N-(2-(4-Aminophenyl)ethyl)-5-chloro-2-methoxybenzamide

A suspension of 13.7 g (46.1 mmol) of the compound of Example 14a) and 60 g (0.27 mol) of SnCl$_2$×2H$_2$O in 400 ml of EA was heated to reflux with stirring for 2 h. After cooling, the reaction mixture was treated with 400 ml of a 10% strength NaHCO$_3$ solution and the deposited precipitate was filtered off with suction. The precipitate was taken up in EA and the aqueous phase was extracted with EA. The combined EA solutions were dried over sodium sulfate and concentrated. Drying of the remaining residue in a high vacuum yielded 12.1 g of the title compound. $R_f$ (silica gel, EA/heptane 4:1)=0.23. MS (DCI): m/z=305 (M+H)$^+$.

c) 5-Chloro-N-(2-(4-iodophenyl)ethyl)-2-methoxybenzamide 9.0 g (29.6 mmol) of the compound of Example 14b) were suspended in a solution of 30 ml of water and 7.5 ml of conc. hydrochloric acid. After cooling the suspension to 0° C., a solution of 2.1 g (30.6 mmol) of sodium nitrite in 6 ml of water was added dropwise. After stirring at 0° C. for 5 min, a solution of 5.0 g (30.6 mmol) of potassium iodide in 7.5 ml of water was then added dropwise and the resulting solution was stirred at room temperature for 1 h and then at 40° C. for 10 min with addition of 40 ml of water. After cooling and after addition of NaHSO$_3$, the solution was extracted a number of times with DCM, and the combined organic phases were washed with water and dried over sodium sulfate. The solvent was removed in vacuo and the residue was purified by chromatography on silica gel using EA/heptane (1:2) as eluent. 5.9 g of the title compound were obtained. $R_f$ (silica gel, EA/heptane 2:1)=0.48. MS (DCI): m/z=415 (M+H)$^+$.

d) 5-(2-(5-Chloro-2-methoxybenzamido)ethyl)-2-iodobenzenesulfonamide

The substance was prepared analogously to Example 1b) using 5.6 g (13.5 mmol) of the compound of Example 14c). 3.3 g of the title compound were obtained. $R_f$ (silica gel, EA/heptane 4:1)=0.35. MS (DCI): m/z=494 (M+H)$^+$.

e) 5-(2-(5-Chloro-2-methoxybenzamido)ethyl)-N-(dimethylaminomethylene)-2-iodobenzenesulfonamide The preparation was carried out from the compound of Example 14d) according to the process mentioned in Example 1c). Starting from 2.2 g (4.4 mmol) of the compound of Example 14d), after purification by chromatography on silica gel using EA/heptane (4:1) as eluent 1.7 g of the title compound were obtained as a white solid. M.p.: 183–186° C. $R_f$ (silica gel, EA/heptane 4:1)=0.14. MS (DCI): m/z=549 (M+H)$^+$.

f) 5-(2-(5-Chloro-2-methoxybenzamido)ethyl)-N-(dimethylaminomethylene)-2-(2-furyl)benzenesulfonamide 0.5 g (0.91 mmol) of the compound of Example 14e) was suspended in 5 ml of absolute THF. 40 mg (0.005 mmol) of bis(triphenylphosphine)-palladium(II) chloride and 450 mg (1.26 mmol) of 2-(tributylstannyl)furan were added successively and the resulting reaction mixture was stirred under reflux for 20 h. After addition of 10 ml of diethyl ether, the reaction solution was filtered through neutral alumina, which was then washed a number of times with diethyl ether and EA. The combined filtrates were [lacuna] twice with water, dried and concentrated. Purification of the resulting residue by chromatography on silica gel using EA/heptane (4:1) as eluent yielded 415 mg of the title compound. $R_f$ (silica gel, EA/heptane 4:1)=0.15. MS (FAB): m/z=490 (M+H)$^+$.

g) 5-(2-(5-Chloro-2-methoxybenzamido)ethyl)-2-(2-furyl)benzenesulfonamide

The preparation was carried out from the compound of Example 14f) according to the process mentioned in Example 1e). Starting from 475 mg (0.91 mmol) of the compound of Example 14f), 280 mg of the title compound resulted as a beige solid. M.p. 195° C. $R_f$ (silica gel, EA/heptane 4:1)=0.42. MS (FAB): m/z=435 (M+H)$^+$.

h) 5-(2-(5-Chloro-2-methoxybenzamido)ethyl)-2-(2-furyl)-N-(methylaminothiocarbonyl)benzenesulfonamide The preparation was carried out from the compound of Example 14g) according to the process mentioned in Example 1f). Starting from 150 mg (0.35 mmol) of the compound of Example 14g), after chromatographic purification on silica gel using DCM/EA (4:1) as eluent, 150 mg of the title compound resulted as pale yellow solid. M.p. 145–146° C. $R_f$ (silica gel, EA/heptane 4:1)=0.25. MS (DCI): m/z=508 (M+H)$^+$.

Example 15

5-(2-(5-Chloro-2-methoxybenzamido)ethyl)-2-(2-furyl)-N-(methylaminocarbonyl)benzenesulfonamide

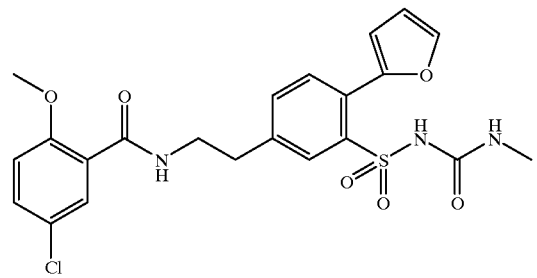

The preparation was carried out from the compound of Example 14h) according to the process mentioned in Example 2). Starting from 80 mg (0.16 mmol) of the compound of Example 14h), 60 mg of the title compound resulted in the form of a white solid. M.p. 118–120° C. $R_f$ (silica gel, EA/heptane 4:1)=0.13. MS (DCI): m/z=492 (M+H)$^+$.

Example 16

5-(2-(5-Chloro-2-methoxybenzamido)ethyl)-N-(methylaminothiocarbonyl)-2-(2-pyridyl)benzenesulfonamide

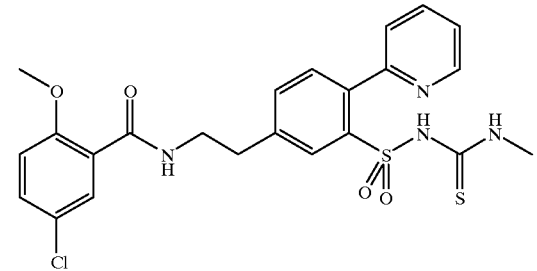

a) 2-(Trimethylstannyl)pyridine

Under an argon atmosphere, 7.5 ml of n-butyllithium (15% strength in hexane, 12 mmol) were added dropwise to a solution of 1.9 g (12.0 mmol) of 2-bromopyridine in 50 ml of absolute THF cooled to −78° C. After stirring at −78° C. for 1 h, 12 ml (12 mmol) of a 1 M solution of trimethyltin chloride in THF were added dropwise and the mixture was stirred at −78° C. for a further hour. The reaction solution was warmed to 0° C. and treated with water. The organic phase was separated off and the aqueous phase was extracted a number of times with diethyl ether. The combined organic phases were dried over sodium sulfate and concentrated. The residue was distilled in vacuo (0.3 bar) in a bulb tube. 1.9 g of the title compound resulted as a colorless oil.

b) 5-(2-(5-Chloro-2-methoxybenzamido)ethyl)-N-(dimethylaminomethylene)-2-(2-pyridyl)benzenesulfonamide 400 mg (0.73 mmol) of the compound of Example 14e) were suspended in 5 ml of absolute THF. 32 mg (0.004 mmol) of bis(triphenylphosphine)palladium(II) chloride, 10 mg of lithium chloride and 199 mg (0.82 mmol) of the compound of Example 16a) were added successively and the resulting reaction mixture was stirred under reflux for 7 h. 10 mg of lithium chloride and 10 mg of copper(I) iodide were added and the mixture was heated to reflux for a further 2 h. After cooling, the reaction solution was treated with 10 ml of EA and filtered, and the filtrate was concentrated. Purification of the resulting residue by chromatography on silica gel using DCM/EA (4:1) as eluent yielded 265 mg of the title compound. $R_f$ (silica gel, DCM/EA 4:1)=0.05. MS (DCI): m/z=501 (M+H)$^+$.

c) 5-(2-(5-Chloro-2-methoxybenzamido)ethyl)-2-(2-pyridyl)benzenesulfonamide

The preparation was carried out from the compound of Example 16b) according to the process mentioned in Example 1e). Starting from 250 mg (0.50 mmol) of the compound of Example 16b), 160 mg of the title compound resulted as a beige solid. M.p.: 202–203° C. $R_f$ (silica gel, DCM/EA 4:1)=0.29. MS (DCI): m/z=446 (M+H)$^+$.

d) 5-(2-(5-Chloro-2-methoxybenzamido)ethyl)-N-(methylaminothiocarbonyl)-2-(2-pyridyl)benzenesulfonamide The preparation was carried out from the compound of Example 16c) according to the process mentioned in Example 1f). Starting from 150 mg (0.34 mmol) of the compound of Example 16c), after chromatographic purification on silica gel using DCM/EA (4:1) as eluent 118 mg of the title compound resulted as a pale yellow solid. M.p.: 85–86° C. $R_f$ (silica gel, EA/heptane 4:1)=0.21. MS (FAB): m/z=519 (M+H)$^+$.

Example 17

5-(2-(5-Chloro-2-methoxybenzamido)ethyl)-N-(methylaminocarbonyl)-2-(2-pyridyl)benzenesulfonamide

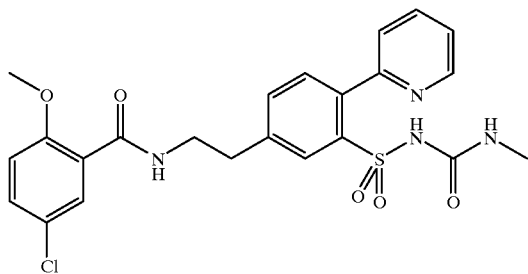

The preparation was carried out from the compound of Example 16d) according to the process mentioned in Example 2). Starting from 75 mg (0.14 mmol) of the compound of Example 16d), 55 mg of the title compound resulted in the form of a white solid. M.p.: 160° C. $R_f$ (silica gel, DCM/EA 4:1)=0.22. MS (FAB): m/z=503 (M+H)$^+$.

Example 18

2-Allyl-5-(2-(5-chloro-2-methoxybenzamido)ethyl)-N-(methylaminocarbonyl)benzenesulfonamide

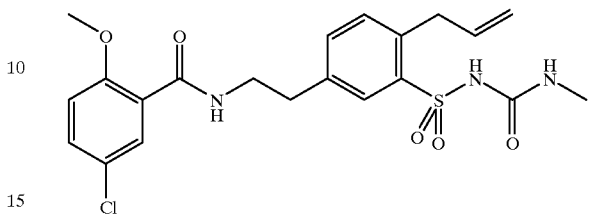

a) 2-Allyl-5-(2-(5-chloro-2-methoxybenzamido)ethyl)-N-(dimethylaminomethylene)benzenesulfonamide The preparation was carried out by reaction of the compound of Example 14e) with allyltributyltin according to the process mentioned in Example 14f). Starting from 800 mg (1.46 mmol) of the compound of Example 14e) and 510 mg (1.65 mmol) of allyltributyltin, after chromatographic purification on silica gel using EA/heptane (4:1) as eluent 600 mg of the title compound were obtained. $R_f$ (silica gel, EA/heptane 4:1)=0.19. MS (FAB): m/z=464 (M+H)$^+$.

b) 2-Allyl-5-(2-(5-chloro-2-methoxybenzamido)ethyl)benzenesulfonamide

The preparation was carried out from the compound of Example 1.8a) according to the process mentioned in Example 1e). Starting from 600 mg (1.30 mmol) of the compound of Example 18a), 460 mg of the title compound resulted as a pale brown solid. M.p.: 186–187° C. $R_f$ (silica gel, EA/heptane 4:1)=0.40. MS (DCI): m/z=409 (M+H)$^+$.

c) 2-Allyl-5-(2-(5-chloro-2-methoxybenzamido)ethyl)-N-(methylaminothiocarbonyl)benzenesulfonamide The preparation was carried out from the compound of Example 18b) according to the process mentioned in Example 1f). Starting from 150 mg (0.37 mmol) of the compound of Example 18b), after chromatographic purification on silica gel using DCM/EA (4:1) as eluent 137 mg of the title compound resulted as a pale yellow solid. M.p.: 164–165°°C. $R_f$ (silica gel, EA/heptane 4:1)=0.19. MS (DCI): m/z=482 (M+H)$^+$.

d) 2-Allyl-5-(2-(5-chloro-2-methoxybenzamido)ethyl)-N-(methylaminocarbonyl)benzenesulfonamide The preparation was carried out from the compound of Example 18c) according to the process mentioned in Example 2). Starting from 68 mg (0.14 mmol) of the compound of Example 18c), 55 mg of the title compound resulted in the form of a white solid. M.p.: 124–126° C. $R_f$ (silica gel, EA/heptane 4:1)=0.12. MS (DCI): m/z=466 (M+H)$^+$.

Example 19

5-(2-(5-Chloro-2-methoxybenzamido)ethyl)-2-ethynyl-N-(methylaminothiocarbonyl)benzenesulfonamide

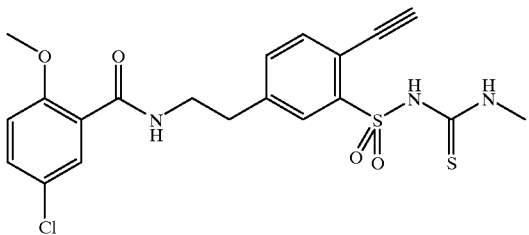

a) 5-(2-(5-Chloro-2-methoxybenzamido)ethyl)-N-(dimethylaminomethylene)-2-ethynylbenzenesulfonamide The preparation was carried out by reaction of the compound of Example 14e) with ethynyltributylstannane according to the process mentioned in Example 14f). Starting from 800 mg (1.46 mmol) of the compound of Example 14e) and 519 mg (1.65 mmol) of ethynyltributylstannane, after chromatographic purification on silica gel using EA/heptane (4:1) as eluent 210 mg of the title compound were obtained. $R_f$ (silica gel, EA/heptane 4:1)=0.10. MS (FAB): m/z=448 (M+H)$^+$.

b) 5-(2-(5-Chloro-2-methoxybenzamido)ethyl)-2-ethynylbenzenesulfonamide

The preparation was carried out from the compound of Example 19a) according to the process mentioned in Example 1e). Starting from 210 mg (0.47 mmol) of the compound of Example 19a), 87 mg of the title compound resulted as an amorphous solid. $R_f$ (silica gel, EA/heptane 4:1)=0.23. MS (DCI): m/z=393 (M+H)$^+$.

c) 5-(2-(5-Chloro-2-methoxybenzamido)ethyl)-2-ethynyl-N-(methylaminothiocarbonyl)benzenesulfonamide The preparation was carried out from the compound of Example 19b) according to the process mentioned in Example 1f). Starting from 87 mg (0.22 mmol) of the compound of Example 19b), 47 mg of the title compound resulted as a white solid. M.p.: 224–225° C., $R_f$ (silica gel, DCM/EA 4:1)=0.18. MS (FAB): m/z=466 (M+H)$^+$.

Example 20

5-(2-(5-Chloro-2-methoxybenzamido)ethyl)-N-(methylaminothiocarbonyl)-2-(phenylsulfanyl)benzenesulfonamide

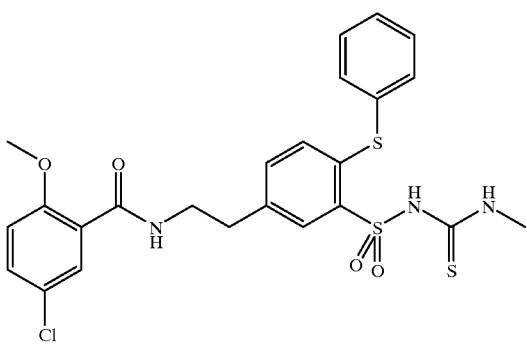

a) 5-(2-(5Chloro-2-methoxybenzamido)ethyl)-N-(dimethylaminomethylene)-2-(phenylsutfanyl)benzenesulfonamide Under an argon atmosphere, 1.7 g (3.1 mmol) of the compound of Example 14e) were added in portions to a suspension of 493 mg (3.73 mmol) of thiophenol sodium salt and 1.17 g (3.1 mmol) of copper(I) iodide in 10.3 ml of hexamethylphosphoramide. The reaction solution was stirred at 80° C. for 6 h. 40 ml of water were then added, the mixture was extracted a number of times with EA and the combined extracts were washed with saturated sodium chloride solution. After drying over sodium sulfate, concentrating and purifying the resulting residue by chromatography on silica gel using EA/heptane (8:1), 700 mg of the title compound were obtained in the form of a white solid. M.p.: 157–158° C., $R_f$ (silica gel, EA/heptane 8:1)=0.40. MS (FAB): m/z=532 (M+H)$^+$.

b) 5-(2-(5-Chloro-2-methoxybenzamido)ethyl)-2-(phenylsulfanyl)benzenesulfonamide The preparation was carried out from the compound of Example 20b) according to the process mentioned in Example 1e). Starting from 300 mg (0.56 mmol) of the compound of Example 20b), 259 mg of the title compound resulted as a white solid. M.p.: 178° C., $R_f$ (silica gel, EA/heptane 8:1)=0.69. MS (DCI): m/z=477 (M+H)$^+$.

c) 5-(2-(5-Chloro-2-methoxybenzamido)ethyl)-N-(methylaminothiocarbonyl)-2-(phenylsulfanyl)benzenesulfonamide The preparation was carried out from the compound of Example 20b) according to the process mentioned in Example 1f). Starting from 252 mg (0.53 mmol) of the compound of Example 20b), 283 mg of the title compound resulted as a white solid. M.p.: 154° C. $R_f$ (silica gel, EA/heptane 20:1)=0.50. MS (DCI): m/z=550 (M+H)$^+$.

Pharmacological Investigations

The therapeutic properties of the compounds of the formula I were demonstrated in the following models.

Test 1: Action potential duration in the papillary muscle of the guinea pig a) Introduction ATP deficiency states, such as are observed during ischemia in the cardiac muscle cell, lead to a reduction of the action potential duration. They are regarded as one of the causes of so-called reentry arrhythmias, which can cause sudden heart death. The opening of ATP-sensitive potassium channels by the lowering of ATP (adenosine triphosphate) is regarded as causing this.

b) Method

A standard microelectrode technique was employed for the measurement of the action potential in the papillary muscle of the guinea pig. For this guinea pigs of both sexes were killed by a blow to the head, the hearts were removed, the papillary muscles were separated out and suspended in an organ bath. The organ bath was irrigated with Ringer's solution (136 mmol/l of NaCl, 3.3 mmol/l of KCl, 2.5 mmol/l of CaCl$_2$, 1.2 mmol/l of KH$_2$PO$_4$, 1.1 mmol/l of MgSO$_4$, 5.0 mmol/l of glucose, 10.0 mmol/l of N-(2-hydroxyethyl)piperazine-N'-(2-ethanesulfonic acid) (HEPES), pH adjusted to 7.4 with NaOH) and aerated with 100% oxygen at a temperature of 37° C. The muscle was stimulated by means of an electrode using squarewave impulses of 1 V and 1 ms duration and a frequency of 1 Hz. The action potential was derived and recorded by means of a glass microelectrode inserted intracellularly, which is filled with 3 mol/l of KCl solution. The substance to be tested was added to the Ringer's solution in a concentration of 2 μmol/l. The action potential was amplified using an amplifier from Hugo Sachs (March-Hugstetten, Germany) and stored and analyzed by means of a computer. The duration of the action potential was determined at a degree of repolarization of 90% ($APD_{90}$). The action potential reduction was produced by addition of a solution of the potassium channel opener rilmakalim (HOE 234) (W. Linz, E. Klaus, U. Albus, R. H. A. Becker, D. Mania, H. C. Englert, B. A. Schölkens, Arzneimittelforschung/Drug Research, 42 (II) (1992) 1180–1185) (rilmakalim concentration 1 µg/ml). 30 minutes after the administration of rilmakalim, the action potential duration $APD_{90}$ was recorded. The test substance was then added and the action potential duration $APD_{90}$, which was extended again, was recorded after a further 60 minutes. The test substances were added to the bath solution as stock solutions in propanediol.

c) Results

The following $APD_{90}$ values (in milliseconds) were recorded.

| Compound | Starting value | +HOE 234, 30 min. | +HOE 234, 30 min., then +substance, 60 min. |
|---|---|---|---|
| Example 1 | 170 | 29 | 134 |
| Example 4 | 165 | 28 | 81 |
| Example 7 | 168 | 24 | 71 |
| Example 13 | 177 | 18 | 72 |
| Example 15 | 171 | 33 | 83 |
| Example 16 | 183 | 32 | 153 |
| Example 20 | 191 | 37 | 139 |

The values found after 60 min confirm the normalizing action of the substances according to the invention on a reduced action potential duration.

Test 2: Membrane potential on isolated β cells a) Introduction

The mechanism of action of the hypoglycemic sulfonylureas such as, for example, glibenclamide has been elucidated in broad outline. The target organ of the sulfonylureas is the β cell of the pancreas, where they contribute to the release of the hypoglycemic hormone insulin by influencing the electrical potential of the cell membrane. A hypoglycemic sulfonylurea such as, for example, glibenclamide brings about a depolarization of the cell membrane, which leads to a decreased influx of calcium ions and as a consequence of this to insulin release. The extent $\Delta U$ of this depolarization of the cell membrane by the test substances was determined on insulin-secreting RINm5F cells, a pancreas tumor cell line. The potency of a compound in this model predicts the extent of the hypotensive potential of this compound.

b) Method

Cell cultures of RINm5F cells: RINm5F cells were cultured at 37° C. in RPMI 1640 culture medium (Flow), to which 11 mmol/l of glucose, 10% (v/v) fetal calf serum, 2 mmol/l of glutamine and 50 µg/ml of gentamycin were added. The cells were inoculated onto petri dishes every 2 to 3 days and kept in a humidified atmosphere of 95% $O_2$ and 5% $CO_2$ at a temperature of 37° C. For the investigations, the cells were isolated by incubation (about 3 min) in a $Ca^{2+}$-free medium which contains 0.25% trypsin.

Measuring method: in a Plexiglas chamber, isolated RINm5F cells were applied to an inverted microscope which was equipped with differential interference contrast optics. Under visual control (400× magnification), a fire-polished micropipette having an opening diameter of approximately 1 µm was placed onto the cell with the aid of a micromanipulator. By applying a slight underpressure to the interior of the patch pipette, a high electrical seal between the glass and cell membrane was first produced. Then, by increasing the underpressure, the membrane spot under the measuring pipette was torn off. In this whole-cell configuration, the cell potential was recorded with the aid of a patch clamp amplifier (L/M EPC 7, List, Darmstadt) and the whole-cell current was measured by applying a voltage ramp. The patch pipette was filled with a KCl solution which contained 140 mmol/l of KCl, 10 mmol/l of NaCl, 1.1 mmol/l of $MgCl_2$, 0.5 mmol/l of EGTA, 1 mmol/l of Mg-ATP, 10 mmol/l of HEPES, and which had a pH of 7.2. An NaCl solution which contained 140 mmol/l of NaCl, 4.7 mmol/l of KCl, 1.1 mmol/l of $MgCl_2$, 2.0 mmol/l of $CaCl_2$, 10 mmol/l of HEPES and which had a pH of 7.4 was situated in the bath. Stock solutions of the test substances in a concentration of 100 mmol/l in DMSO and corresponding dilutions in an NaCl solution were prepared. DMSO on its own had no effect on the cell potential. In order to stabilize the cell potential, diaxozide (100 µmol/l), an opener for ATP-sensitive $K^+$ channels, was added to the bath solution in all experiments. All experiments were carried out at 34±1° C.

c) Results

The following values AU, that is changes (depolarizations) of the cell potentials brought about by the addition of the test substances, were measured. The control values mentioned are the cell potentials U before the addition of the test substances. For comparison, the values are indicated which were obtained in this test using glibenclamide, a typical hypoglycemic benzenesulfonylurea.

| Compound | Concentration | ΔU | Control value |
|---|---|---|---|
| Example 1 | 1 µmol/l | 6 mV | −74 mV |
| Example 9 | 1 µmol/l | 15 mV | −74 mV |
| Example 12 | 1 µmol/l | 5 mV | −78 mV |
| Example 14 | 1 µmol/l | 7 mV | −70 mV |
| Glibenclamide | 1 µmol/l | 47 mV | −73 mV |

The values found confirm that the substances according to the invention have no or only a slight hypoglycemic action.

What is claimed is:

1. A compound of the formula I

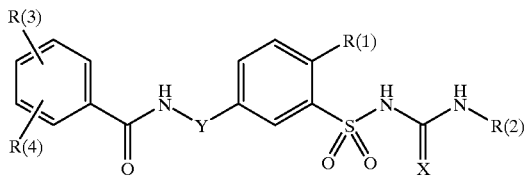

in any stereoisomeric form, or a physiologically tolerable salt thereof, or a mixture thereof in any ratio, in which X is oxygen or sulfur;

Y is —$(CR(5)_2)_n$—;

R(1) is
  a) phenyl which is unsubstituted or is substituted by one or two identical or different substituents independently representing halogen, ($C_1$–$C_4$)-alkyl, ($C_1$–$C_4$)-alkoxy, —$S(O)_m$—($C_1$–$C_4$)-alkyl, phenyl, amino, hydroxyl, nitro, trifluoromethyl, cyano, hydroxycarbonyl, carbamoyl, ($C_1$–$C_4$)-alkoxycarbonyl or formyl; or b) naphthyl; or c) monocyclic or bicyclic heteroaryl having one ring heteroatom representing oxygen, sulfur or nitrogen; or d) —S(O)$_m$-phenyl; or e) (C$_2$–C$_5$)-alkenyl which is unsubstituted or is substituted by a radical representing phenyl, cyano, hydroxycarbonyl or (C$_1$–C$_4$)-alkoxycarbonyl; or f) (C$_2$–C$_5$)-alkynyl which is unsubstituted or is substituted by a radical representing phenyl or (C$_1$–C$_4$)-alkoxy;

R(2) is hydrogen or (C$_1$–C$_3$)-alkyl;

R(3) and R(4) independently of one another are hydrogen, halogen or (C$_1$–C$_4$)-alkoxy;

the radicals R(5), which are all independent of one another and can be identical or different, are hydrogen or (C$_1$–C$_3$)-alkyl;

m is 0, 1 or 2;

n is 1, 2, 3 or 4.

2. A compound as claimed in claim 1, in which R(1) is a) phenyl which is unsubstituted or is substituted by a substituent representing halogen, (C$_1$–C$_4$)-alkyl, (C$_1$–C$_4$)-alkoxy, —S(O)$_m$—(C$_1$–C$_4$)-alkyl, trifluoromethyl or nitro; or b) monocyclic heteroaryl having one ring heteroatom representing oxygen, sulfur or nitrogen; or c) —S-phenyl; or d) (C$_2$–C$_3$)-alkenyl; or e) ethynyl or 2-phenylethynyl.

3. A compound as claimed in claim 1, in which R(2) is (C$_1$–C$_3$)-alkyl.

4. A compound as claimed in claim 1, in which Y is —(CH$_2$)$_n$—.

5. A compound as claimed in claim 1, which is of the following formula:

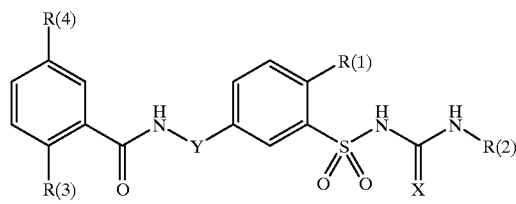

in which

Y is —CH$_2$—CH$_2$—;

R(2) is methyl, ethyl or isopropyl;

R(3) is (C$_1$–C$_4$)-alkoxy; and

R(4) is halogen.

6. A process for the preparation of a compound of the formula I as claimed in claim 1, which comprises reacting a compound of formula VIII

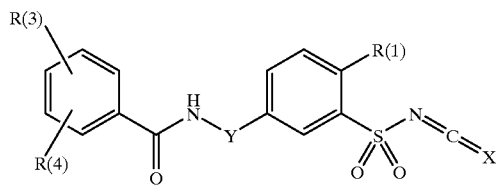

with an amine of the formula R(2)—NH$_2$, where R(1), R(2), R(3), R(4), X and Y have the meanings indicated in claim 1, to obtain the compound of formula I.

7. A pharmaceutical composition, which comprises one or more compounds as claimed in claim 1 and a pharmaceutically tolerable carrier.

8. A method for the therapy or prophylaxis of a cardiovascular disorder, an ischemic condition of the heart a weakened myocardial contractile force, or cardiac arrhythmia, which comprises administering to a host in need of the therapy or prophylaxis an effective amount of a compound as claimed in claim 1.

9. A process for the preparation of a compound of the formula I as claimed in claim 1 in which X is sulfur, which comprises reacting a benzenesulfonamide of the formula III

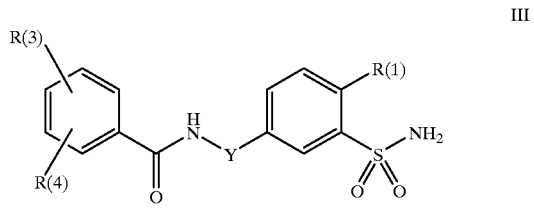

or a salt thereof with an R(2)-substituted isothiocyanate of the formula R(2)—N=C=S, where R(1), R(2), R(3), R(4) and Y have the meanings indicated in claim 1, to obtain the compound of formula I.

10. A process for the preparation of a compound of the formula I as claimed in claim 1 in which X is oxygen, which comprises reacting a benzenesulphonamide of the formula III

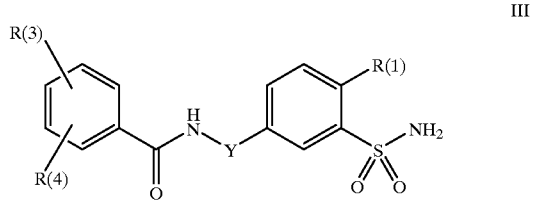

or a salt thereof with an R(2)-substituted isocyanate of the formula R(2)—N=C=O or with an R(2)-substituted 2,2,2-trichloroacetamide of the formula Cl$_3$C—CO—NH—R(2), where R(1), R(2), R(3), R(4) and Y have the meanings indicated in claim 1, to obtain the compound of formula I.

11. A process for the preparation of a compound of the formula I as claimed in claim 1 in which X is oxygen, which comprises desulfurizing a corresponding compound of the formula I in which X is sulfur on the thiourea group to obtain the compound of formula I in which X is oxygen.

* * * * *